United States Patent
Amblard et al.

(10) Patent No.: US 9,061,069 B2
(45) Date of Patent: Jun. 23, 2015

(54) USE OF CONSTRAINED PEPTIDE MIMIC OLIGOMERS AS VECTORIZATION AGENTS

(75) Inventors: Muriel Amblard, Saint Vincent de Barbeyrargues (FR); Jean Martinez, Caux (FR); Lubomir Vezenkov, Montpellier (BG); Jean-Francois Hernandez, Gignac (FR); Marcel Garcia, Prades le Lez (FR); Marie Maynadier, Auribeau (FR)

(73) Assignees: CENTRE NATIONAL DE LA RECHERCHE SCIENTIFIQUE, Paris (FR); UNIVERSITE DE MONTPELLIER 1, Montpellier (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 13/388,114

(22) PCT Filed: Aug. 2, 2010

(86) PCT No.: PCT/EP2010/061229
§ 371 (c)(1),
(2), (4) Date: Jan. 31, 2012

(87) PCT Pub. No.: WO2011/012729
PCT Pub. Date: Feb. 3, 2011

(65) Prior Publication Data
US 2012/0184480 A1 Jul. 19, 2012

(30) Foreign Application Priority Data
Jul. 31, 2009 (FR) ...................................... 09 55427

(51) Int. Cl.
*A61K 47/34* (2006.01)
*A61K 47/48* (2006.01)

(52) U.S. Cl.
CPC ........... *A61K 47/48246* (2013.01); *A61K 47/34* (2013.01); *A61K 47/48315* (2013.01)

(58) Field of Classification Search
None
See application file for complete search history.

(56) References Cited

U.S. PATENT DOCUMENTS

2003/0191049 A1* 10/2003 Amblard et al. ................... 514/2

OTHER PUBLICATIONS

Porter, E. A. et al; "Non-haemolytic beta-amino acid oligomers." Nature (2000) 404 p. 565.*
Turner, Laura H. et al; "Antisocial and seizure susceptibility phenotypes in an animal model of epilepsy are normalized by impairment of brain corticotropin releasing factor." Epilepsy and Behavior (2007) 10 p. 8-15.*
Porter, Emilie A. et al; "Non-haemolytic beta amino acid oligomers." Nature (2000) 404 p. 565.*
Turner, Laura H. et al; Antisocial and seizure susceptibility phenotypes in an animal model of epilepsy are normalized by impairment of brain corticotropin releasing factor. Epilepsy and Behavior (2007) 10 p. 8-15.*
McGregor, Duncan Patrick; "Discovering and improving novel peptide therapeutics" Curr. Opin. Pharmacol. (2008) 8 p. 616-619.*
Songis, Olivier et al; "Ayymmetric diels-alder reaction of aminodienes with a nonracemic acrylate bound to rink resin: a comparison of those reactions with their solution state analogues." Eur. J. Org. Chem. (2008) 2 p. 308-318.*
Stewart, Barbra H. And Chan, O. Hellen; "Use of immobilized artificial membrane chromatography for drug transport applications." J. Pharmaceut. Sci. (1998) 87(12) p. 1471-1478.*
Crane, R. K.; "THe graident hypothesis and other models of carrier mediated active transport." Rev. Physiol. Biochem. Pharmacol. (1977) 78 p. 101-161.*
Ghosh, R. N. et al; "Cell-based, high-content screen for receptor internalization, recycling and intracellular trafficing." Biotechniques (2000) 29 p. 170-175.*
Futaki, Shiroh; "Membrane-permeable arginine-rich peptides and the translocation mechanisms." Adv. Drug. Deliv. Rev. (2005) 57 p. 547-558.*
Fernández-Carneado, J. et al; "Fatty acyl moieties: improving pro-rich peptide uptake inside hela cells." J. Peptide. Red. (2005) 65(6) p. 580-590.*
The GenBank entry P02452, downloaded Jun. 5, 2014.*
Epstein, Ervin H. and Munderloh, Neil H.; "Isolation and characterization of cnbr peptides of human [alpha1 (iii)] 3 collagen and tissue distribution of [alpha1(1)]2alpha2 and [alpha1(III)]3 collagens." J. Biol. Chem. (1975) 250(24) p. 9304-0312.*
Holladay, Mark W. et al; "Synthesis and biological activity of cck heptapeptide analogues. Effects of conformational constraints and standard modifications on receptor subtype selectivity, functional activity in vitro, and appetite supression in vivo." J. Med. Chem. (1992) 35(16) p. 2019-2028.*
Teale, F. W. J. and WEber, G.; "Ultraviolet fluorescence of the aromatic amino acids." Biochem. J. (1957) 65 p. 476-482.*
Freidinger, Roger M. et al; "Lactam restriction of peptide conformation in cyclic hexapeptides which alter rumen fermentation." Int. J. Peptide Protein Res (1980) 16 p. 464-470.*
Evin, Genevieve et al; "Aspartyl protease inhiibtor pepstatin binds to the presenilins of alzheimer's disease." Biochemistry (2001) 40 p. 8359-8368.*
Brown, Michael S. et al; "Regulated intramembrane proteolysis: a control mechanism conserved from bacteria tohumans." Cell (2000) 100 p. 391-398.*
Ballet et al., "Blood-Brain Barrier Penetration by Two Dermorphin Tetrapeptide Analogues: Role of Lipophilicity vs. Structural Flexibility", J. Med. Chem., vol. 51 (2008) pp. 2571-2574.
Farrera-Sinfreu et al., "Cell-Penetrating Proline-Rich Peptidomimetics", Methods in Molecular Biology, vol. 386 (2007) pp. 241-267.
Heitz et al., "Twenty years of cell-penetrating peptides: from molecular mechanisms to therapeutics", British Journal of Pharmacology, vol. 157 (2009) pp. 195-206.
Pujals et al, "Proline-rich, amphipathic cell-penetratng peptides", Advanced Drug Delivery Reviews, vol. 60 (2007) pp. 473-484.

* cited by examiner

*Primary Examiner* — Maury Audet
*Assistant Examiner* — Fred Reynolds
(74) *Attorney, Agent, or Firm* — Birch, Stewart, Kolasch & Birch, LLP

(57) ABSTRACT

The invention relates to the use of oligomers having constrained dipeptide or tripeptide motifs as agents for the vectorization of active ingredients.

21 Claims, 3 Drawing Sheets

USE OF CONSTRAINED PEPTIDE MIMIC OLIGOMERS AS VECTORIZATION AGENTS

Figure 1:
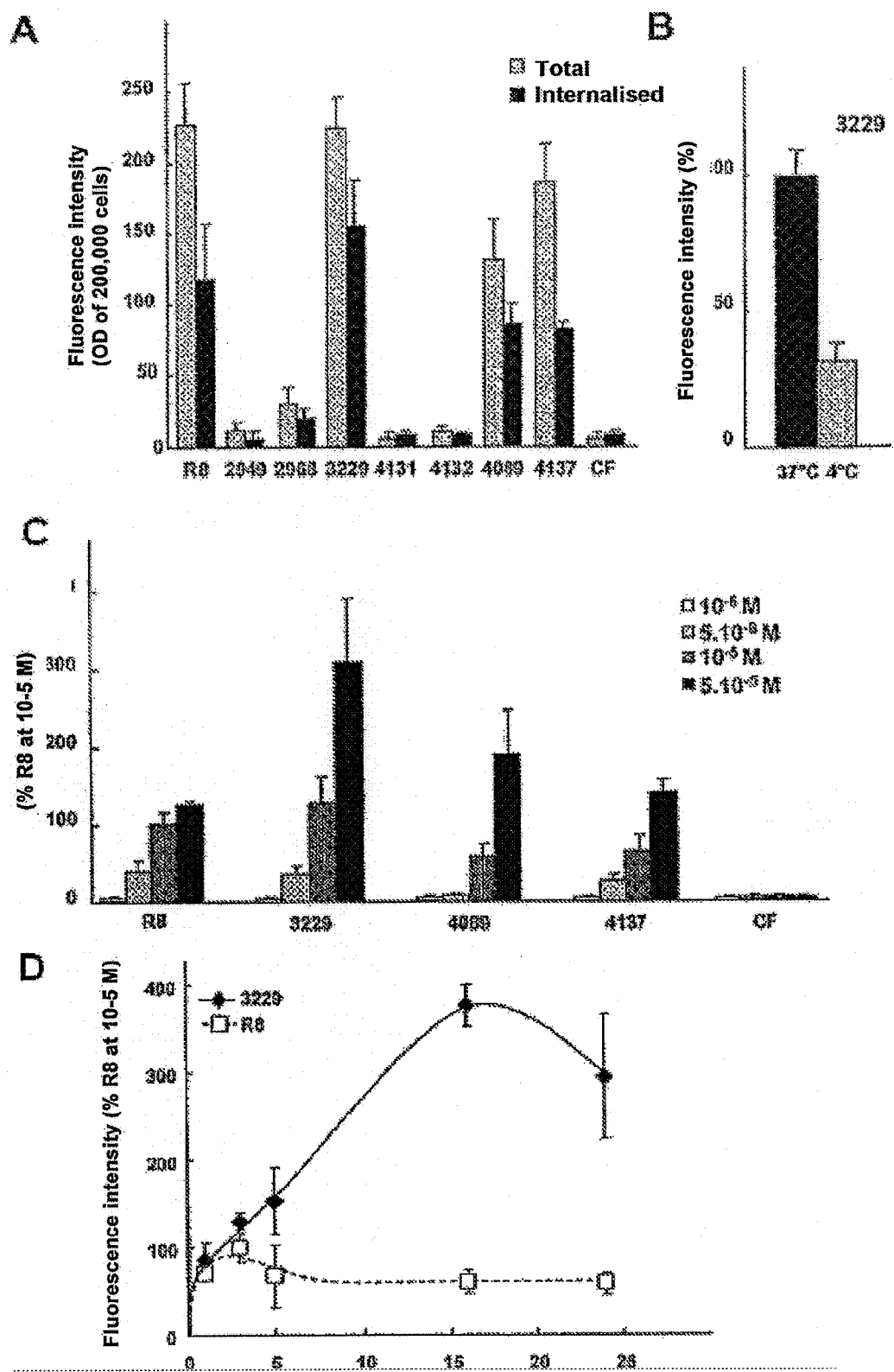

The present invention relates to a novel class of compounds capable of penetrating into biological cells and transporting therein molecules of interest, such as medicines or biological probes.

More specifically, the invention relates to the use of oligomers having constrained dipeptide and tripeptide motifs as vectorization agents.

The problem of the transport of active substances through the plasma membrane and their access to the various intracellular compartments is currently a major problem in a large number of therapies (anticancer, antiviral for example).

Indeed, and even if lipophilicity is a factor of capture by the membrane, the molecule is not guaranteed to pass through said membrane to access the cytoplasm. Among the means currently used to introduce substances into cells, translocation peptides named CPP for "Cell-Penetrating-Peptides" (Advanced Drug Delivery Reviews, Volume 60, Numbers 4-5, Pages 447-614 (1 Mar. 2008), Membrane Permeable Peptide Vectors: Chemistry and Functional Design for the Therapeutic Applications, Edited by S. Futaki) are the vectors the most used. Over the last ten or so years, said vectors are the subject of numerous studies for the interest that they exhibit in the vectorization of anti-tumorals, antisense oligonucleotides, peptide nucleic acid (PNA), small interfering RNA (siRNA), peptides or proteins.

Nevertheless, the stability of said compounds of peptidic nature vis-à-vis proteases implies a risk of rapid destruction of the vector/active molecule conjugate in vivo. Finally, the hydrophilic character of molecules of poly-cationic type, generally used in this field, does not enable the translocation of medicines through certain physiological barriers such as the hemato-encephalic barrier.

All of these reasons make essential the development of novel vectors both for fundamental research (understanding of internalisation mechanisms) and for therapeutic or diagnostic uses.

Thus, and although the field of vectorization of molecules of interest already makes available a certain number of compounds, certain points need to be resolved, among which bioavailability, toxicity, a specific addressing of the intracellular compartments and feasibility at an industrial scale.

The subject of the present invention aims to resolve some of these problems. It implies the use of an oligomer described previously (WO 01/51506) to vectorize molecules of interest. Said oligomers are known to be polypeptide or protein mimics. Said polypeptide or protein mimics are more stable than their natural analogues from which they differ by their structure, particularly by size. Moreover, an oligomer constituted of only several monomers, bonded to a molecule of interest, is capable of passing through a plasma membrane.

SUMMARY OF THE INVENTION

The present invention relates to the use of an oligomer of formula (I'):

$$—X_1—(NR_1—R\text{-}A\text{-}R'—CO)_n—X_2—$$ (I')

to prepare a vectorized active ingredient (AI) of formula (I) by bonding (AI) to $X_1$ and/or $X_2$ in order to facilitate the entry of said active ingredient into biological cells, in which the recurrent units —(NR$_1$—R-A-R'—CO)— and the terms $X_1$, $R_1$, R, A, R', $X_2$ and n are as defined below.

The recurrent units —(NR$_1$—R-A-R'—CO)—, independently identical or different to each other, represent constrained dipeptide or tripeptide mimics, advantageously beta turn inducers.

The number of recurrent units —(NR$_1$—R-A-R'—CO)— of the oligomer is defined by the number n; n is a whole number comprised between 2 and 40.

In the recurrent unit —(NR$_1$—R-A-R'—CO)— of the formula (I'), the terms R and R', independently of each other, represent a bond or a $C_1$-$C_6$ alkyl group optionally substituted by an aryl group or by a side chain of an amino acid.

In the recurrent unit —(NR$_1$—R-A-R'—CO)— of the formula (I'), the term A represents a hydrocarbon cycle or a heterocycle, monocyclic or polycyclic, saturated or unsaturated, comprising one or more cycles from 3 to 10 atoms each and a total number of cycles not exceeding 3, optionally substituted by one or more groups selected from the group constituted of $C_1$-$C_6$ alkyl, oxo (=O), nitrile, —C(=NH)NH$_2$, —NH—C(=NH)NH$_2$, —(CH$_2$)$_u$OH, —CO$_2$H, —CONH$_2$, F, CF$_3$, —(CH$_2$)$_v$NH$_2$, and/or —CONH(CH$_2$)$_w$NH$_2$, u, v and w being whole numbers comprised between 0 and 10.

In the recurrent unit —(NR$_1$—R-A-R'—CO)— of the formula (I'), the term $R_1$ represents a hydrogen atom or instead $R_1$ forms a cycle with the nitrogen atom to which it is bonded, said cycle being either condensed with the group A, or bonded to the group A by a $C_1$-$C_6$ alkyl, or bonded to A by a spiro junction.

In the formula (I'), the terms $X_1$ and $X_2$, independently of each other, represent a spacer group or a bond.

Another subject of the present invention relates to the oligomer represented by the generic formula (I):

$$R_6—X_1—(NR_1—R\text{-}A\text{-}R'—CO)_n—X_2—R_7$$ (I)

in which the recurrent units —(NR$_1$—R-A-R'—CO)—, and the terms n, R, R', A, $R_1$, $X_1$ and $X_2$ are as defined for the formula (I') and one at least of $R_6$ and $R_7$ is an active ingredient (AI) or a marker. In the case where $R_6$ is an active ingredient or a marker, $R_7$ is selected from the groups hydroxy, $C_1$-$C_6$ alkoxy, aryl-($C_1$-$C_6$ alkoxy)-, or NH$_2$ or $R_7$ represents an active ingredient or a marker identical or different to $R_6$. In the case where $R_7$ is an active ingredient or a marker, $R_6$ is selected from a hydrogen atom, a $C_1$-$C_6$ alkyl group, an aryl group —($C_1$-$C_6$ alkyl)-, or $R_6$ is an active ingredient or a marker identical or different to $R_7$.

Another subject of the present invention relates to a method of synthesis to obtain the oligomer of formula (I). The techniques used are similar to those used in peptide synthesis.

Another subject of the present invention relates to the oligomer of formula (I) used as medicine.

Finally, another subject of the present invention is the use of the oligomer of formula (I) to facilitate the entry of an active ingredient (AI) or a marker into biological cells.

DEFINITIONS

"Constrained mimics" are molecular fragments that make it possible to induce artificially secondary structures, such as α helices, β layers or β turns, found in macromolecules such as proteins.

A "dipeptide" is a polymer fragment of two amino acids bound together by an amide bond, also known as peptide bond, stemming from a condensation between the amine of a first amino acid and the carboxylic acid of a second amino acid. A "tripeptide" is constituted of 3 amino acids bonded together by two peptide bonds.

"$C_1$-$C_6$ alkyl" group is taken to mean a saturated hydrocarbon chain, linear or branched, comprising from 1 to 6 carbon atoms, such as for example a methyl, ethyl, isopropyl, tertiobutyl, pentyl group, etc.

"Aryl" group is taken to mean an aromatic group, preferably comprising from 5 to 10 carbon atoms, comprising one or more cycles and comprising optionally one or more heteroatom(s) in particular an oxygen, a nitrogen or a sulphur, such as for example a phenyl, furan, indole, pyridine, naphthalene group, etc.

The term "side chain of an amino acid" represents the fragment borne by the α carbon of an amino acid. For example, the side chains of natural amino acids such as glycine, valine, alanine and aspartic acid correspond to the hydrogen atom, to the isopropyl, methyl and $CH_2COOH$ groups respectively.

The term natural amino acid represents among others the following amino acids: glycine (Gly), alanine (Ala), valine (Val), leucine (Leu), isoleucine (Lie), serine (Ser), threonine (Thr), phenylalanine (Phe), tyrosine (Tyr), tryptophan (Trp), cysteine (Cys), methionine (Met), proline (Pro), hydroxyproline, aspartic acid (Asp), asparagine (Asn), glutamine (Gln), glutamic acid (Glu), histidine (His), arginine (Arg), ornithine, and lysine (Lys).

The side chains of other amino acids may be included in the definition, such as those of the following amino acids: 4-amino tetrahydropyran-4-carboxylic acid, allylglycine, diamino butyric acid, diamino propionic acid, aminoserine, aminobutyric acid, amino butylglycine, phenylglycine, 4-chloro-phenylalanine, 4-nitro-phenylalanine, citrulline, cyclohexylalanine, thienylalanine, and their kind.

The side chains of the amino acids may be protected by protector groups (P) and more particularly N-protectors, O-protectors or S-protectors when these chains contain the corresponding heteroatoms.

The protector groups (P) are groups known to those skilled in the art. Said protector groups and their use are described in works such as for example Greene, "Protective Groups in Organic Synthesis", Wiley, New York, 2007 4th edition; Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. 25 E 22b, Vol. E 22c, Vol. E 22d., M. Goodmann Ed., Georg Thieme Verlag, 2002. Depending on whether said protector groups are borne by a nitrogen atom, they will be designated as N-protector groups. The same is true for the S-protector, O-protector groups, etc. For example, a hydroxy may be protected by a trityl group, or a carboxylic acid may be protected in the form of a tert-butylic ester. If a synthesis is carried out on solid support, it is the resin that serves as protector group to the C-terminal carboxylic function.

The protection of the amino group of the amino acid may be carried out for example by a tert-butyloxycarbonyl group (hereafter designated Boc-) or a -9-fluorenylmethyloxycarbonyl group (hereafter designated Fmoc) represented by the formula:

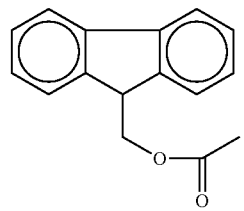

The protection is carried out according to known methods of the prior art. For example, the protection by the Boc-group may be obtained by making the amino acid react with di-tert-butylpyrocarbonate ($Boc_2O$).

The term "monocyclic or polycyclic saturated hydrocarbon cycle" represents equally well in the present invention saturated hydrocarbon groups comprising one or more cycles, advantageously 1, 2 or 3 cycles, each of the cycles comprising from 3 to 10 carbon atoms inscribed in said cycle.

The term "monocyclic or polycyclic unsaturated hydrocarbon cycle" represents equally well in the present invention unsaturated hydrocarbon groups comprising one or more cycles, advantageously 1, 2 or 3 cycles, with at least one of the cycles comprising at least one unsaturation, each of the cycles comprising from 3 to 10 carbon atoms inscribed in said cycle. Moreover, the term "monocyclic or polycyclic unsaturated hydrocarbon cycle" comprises cyclic aromatic groups, in other words aryls, defined above.

In the case where the polycyclic group comprises 2 cycles, said cycles may be merged, bridged, bonded to each other by a spiro junction, or one of the carbon atoms of one of the cycles forms a covalent bond with a carbon atom of the other cycle.

For example, a hydrocarbon bicyclic group in which each cycle is a cycle constituted of 6 carbon atoms may be condensed in the following manner:

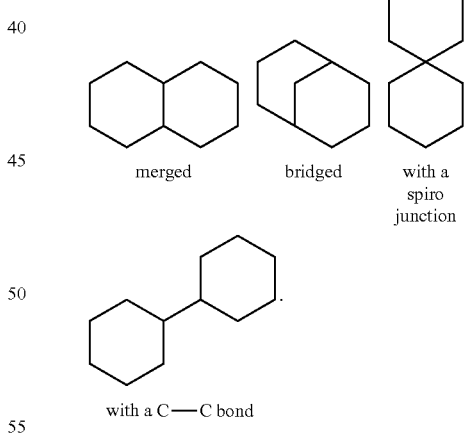

merged     bridged     with a spiro junction with a C——C bond

In the case where the polycyclic group comprises more than 2 cycles, those skilled in the art will understand that a combination of these configurations of cycles can exist.

It must also be understood that one or more of these cycles may be heterocyclic, which means that the cycles incorporate one or more heteroatoms, selected advantageously from the atoms of nitrogen, of oxygen, sulphur.

Examples of hydrocarbon or heterocyclic, mono or polycyclic cycles, saturated or unsaturated, comprise cyclopentyl, cyclohexyl, cycloheptyl, adamantyl, piperidinyl or norbornyl groups.

A "spacer group" according to the invention is a molecular fragment making it possible to attach the oligomer —NR$_1$—R-A-R'—CO— to an active ingredient (AI). Advantageously, the spacer group makes it possible to reduce the steric hindrance between the oligomer and the active ingredient. More advantageously, the spacer group makes it possible to release the active ingredient in the target organite(s) of the biological cell—for example in the lysosome, the mitochondria or the Golgi apparatus. The spacer group is constituted of at least two atoms that can be identical or different.

Advantageously, the spacer group is a sequence of groups limited in size between 1-50 atoms in total, which makes it possible to move the active ingredient or marker away from the oligomer.

Advantageously, the spacer group is a hydrocarbon chain comprising one or more groups selected from: $C_1$-$C_6$ alkyl, aryl, aryl-($C_1$-$C_6$ alkyl), monocyclic or polycyclic saturated hydrocarbon cycle, monocyclic or polycyclic unsaturated hydrocarbon cycle, $C_1$-$C_6$ alkoxy, aryl-($C_1$-$C_6$ alkoxy), amino acids, optionally substituted by one or more hydrogen atoms or by one or more $C_1$-$C_4$-alkyls.

Advantageously, the spacer group is ethylene glycol or a polyethylene glycol, or a peptide or an amino acid which may optionally be substituted. Advantageously, in the case where the spacer group is a polyethylene glycol, said polyethylene glycol comprises from 2 to 10 ethylene glycol units. Advantageously, in the case where the spacer group is a peptide, this comprises from 2 to 15 amino acids, more advantageously from 2 to 10 amino acids and even more advantageously from 2 to 8 amino acids.

Advantageously in the case where the spacer group is an amino acid, said spacer group is an amino acid in which the carboxylic acid and amine functions are separated by a hydrocarbon chain comprised between 2 and 10 carbon atoms, a protease substrate, a disulphide bridge. The two latter spacers make it possible release the active ingredient, the first by cleavage by a target protease and the second by reduction (glutathione system). Other techniques of releasing active ingredients, known to those skilled in the art, may be applied to the present invention.

Advantageously the spacer group comprises or consists in a hydrophilic group. Such hydrophilic groups may include amino acids of the series L or the series D, natural or non natural, and enable a better solubility of the vectorized active ingredient. For example amino acids known to aid solubilization, such as arginine and/or lysine, may be inserted. Advantageously, said amino acids are of the series D so that said additional groups are not easily hydrolysed in vivo.

In a particular embodiment of the invention, the spacer group comprises at least one amino acid.

In a particular embodiment of the invention, the spacer group consists of amino acids.

In a particular embodiment of the invention, the spacer group comprises "-D-Arg-O$_2$Oc-" in which D-Arg represents D-Arginine, O$_2$Oc represents 8-amino-3,6-dioxaoctanoyl.

In a particular embodiment of the invention, the spacer group consist of "-D-Arg-O$_2$Oc-" in which D-Arg represents D-Arginine, O$_2$Oc represents 8-amino-3,6-dioxaoctanoyl.

In a particular embodiment of the invention, the spacer group comprises "-D-Lys-O$_2$Oc-" in which D-Lys represents D-Lysine, O$_2$Oc represents 8-amino-3,6-dioxaoctanoyl.

In a particular embodiment of the invention, the spacer group consists of "-D-Lys-O$_2$Oc-" in which D-Lys represents D-Lysine, O$_2$Oc represents 8-amino-3,6-dioxaoctanoyl.

Techniques for aiding the solubilization/solubility of active ingredients are well known to those skilled in the art and applicable to the compounds of formula (I) by acting at the level of the spacer groups.

"$C_1$-$C_6$ alkoxy" group is taken to mean, according to the present invention, a $C_1$-$C_6$ alkyl group, as defined above, bonded to the molecule through the intermediary of an oxygen atom. As an example, methoxy, ethoxy, propoxy, isopropoxy, butoxy or instead tert-butoxy groups may be cited.

"tBu" designates tert-butyl.

"Aryl-($C_1$-$C_6$ alkoxy)" group is taken to mean, according to the present invention, an aryl group, as defined above, bonded to the molecule through the intermediary of a $C_1$-$C_6$ alkoxy group. As an example, benzyloxy, phenylethoxy, or instead phenylpropoxy groups may be cited.

"Aryl-$C_1$-$C_6$ alkyl)" group is taken to mean, according to the present invention, an aryl group, as defined above, bonded to the molecule through the intermediary of a $C_1$-$C_6$ alkyl group. As an example, benzyl, phenyl-ethyl, phenyl-propyl groups may be cited.

DETAILED DESCRIPTION

The recurrent units —(NR$_1$—R-A-R'—CO)— in the formulas (I) and (I') may comprise one or more asymmetric centres, which may be of configuration R or of configuration S.

In said recurrent units —(NR$_1$—R-A-R'—CO)—, the term "A" represents a hydrocarbon cycle, aromatic or not, or a heterocyclic group, aromatic or not, monocyclic or condensed polycyclic.

As examples of —(NR$_1$—R-A-R'—CO)— groups that exhibit properties of constrained dipeptide or tripeptide mimics and which may be β turn inducers, the following groups may be cited:

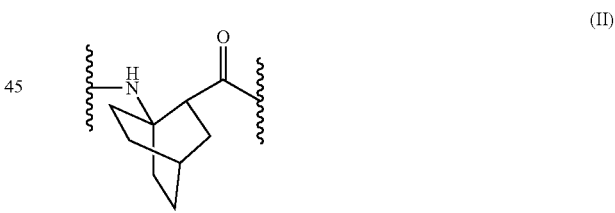

(II)

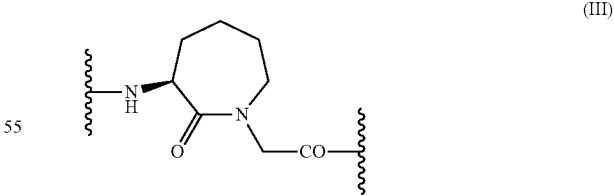

(III)

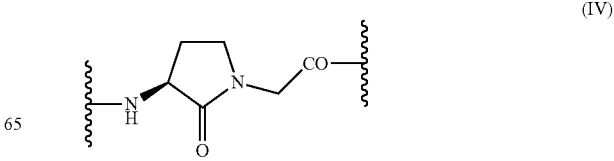

(IV)

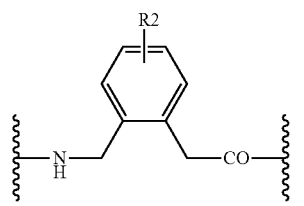
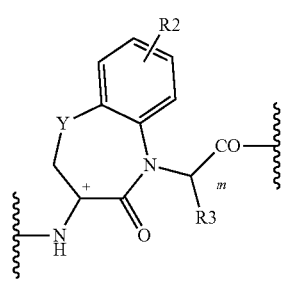
Y = O
NH
S
CH₂
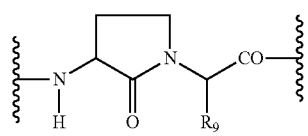
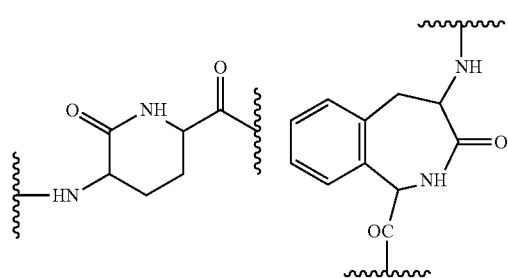
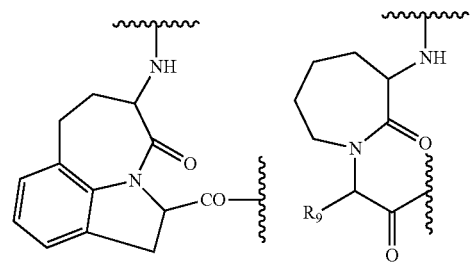
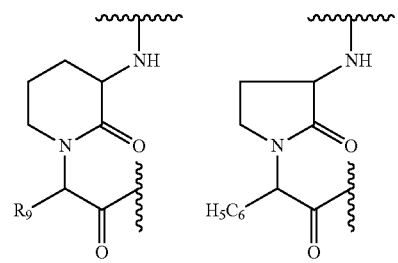
(V)
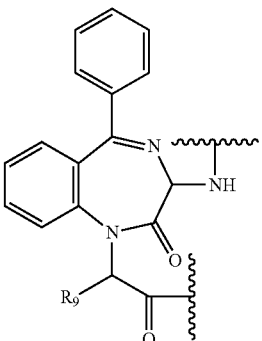
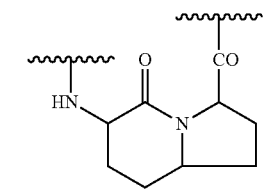
(VI)
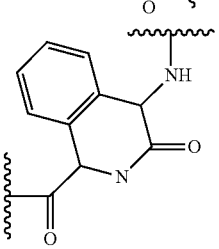
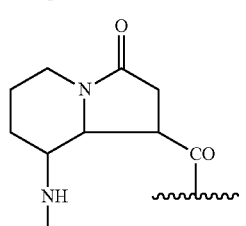
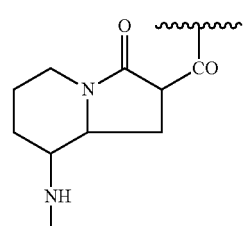
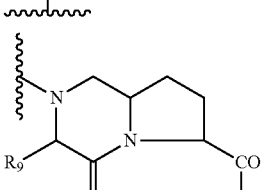
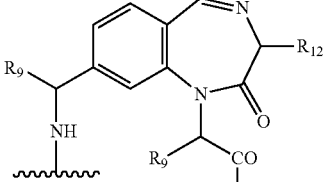
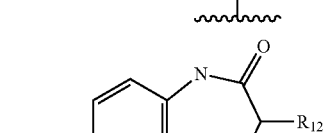
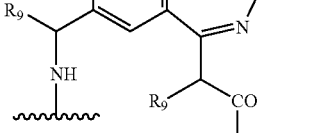
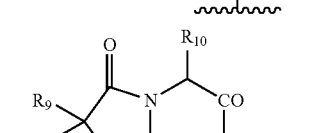

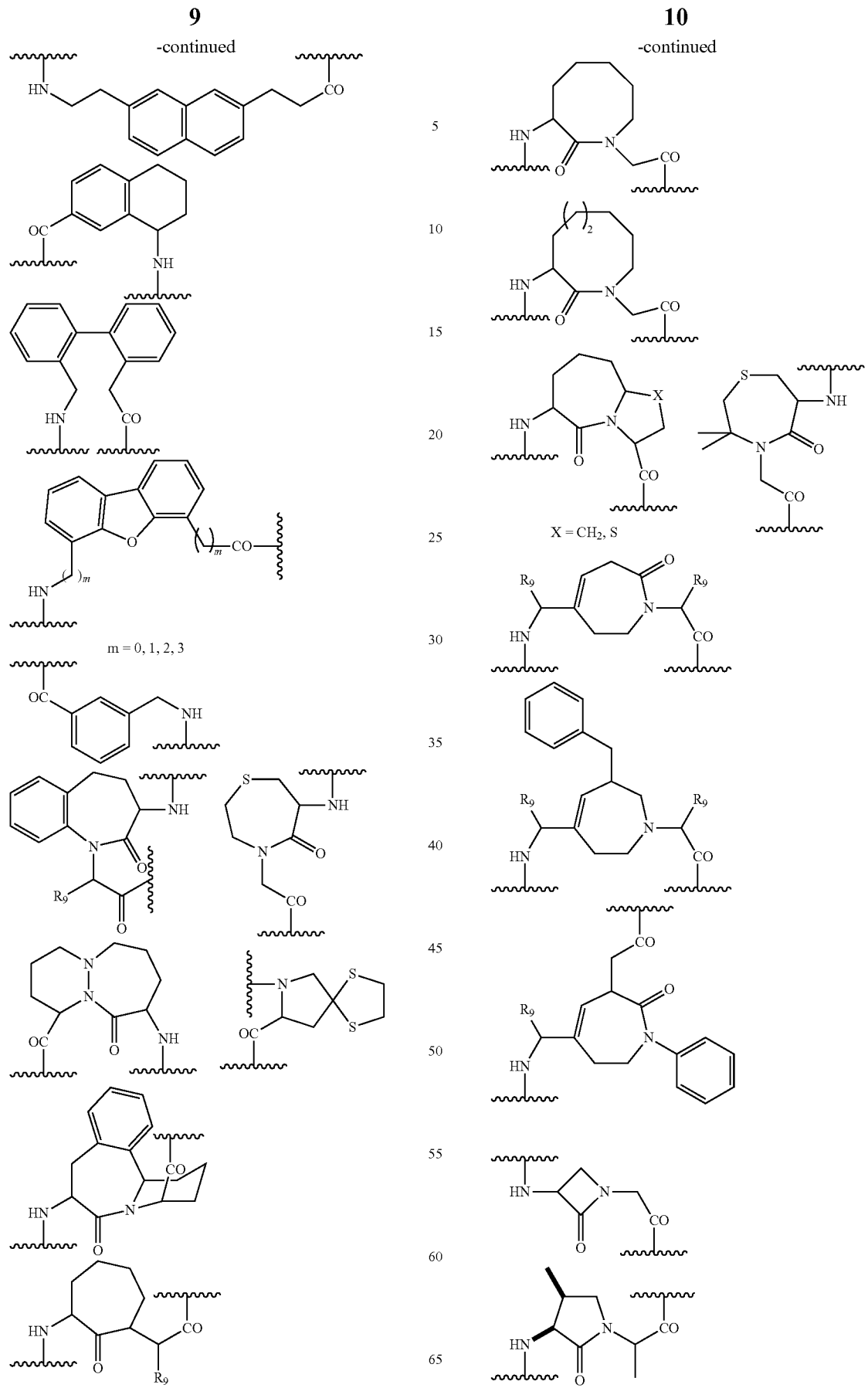

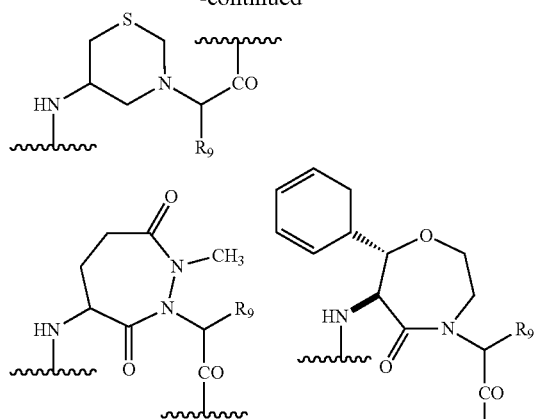
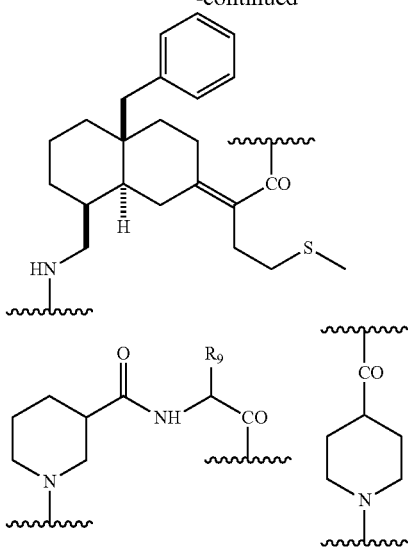
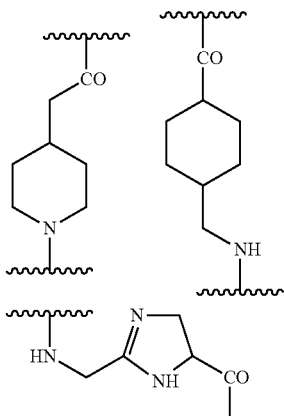
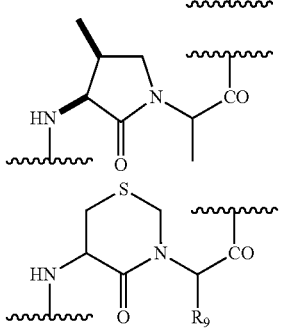
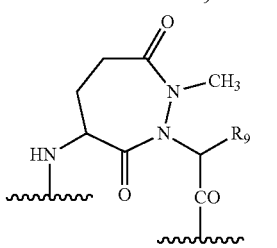
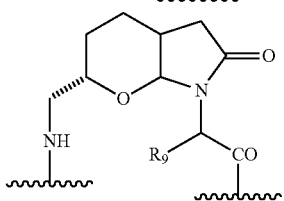

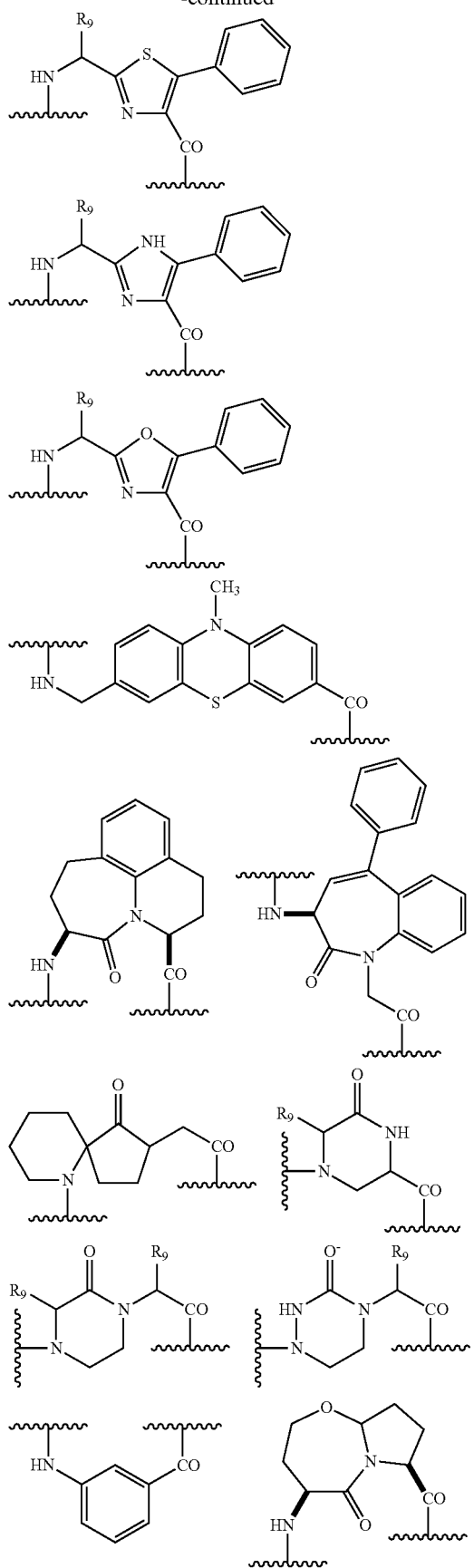
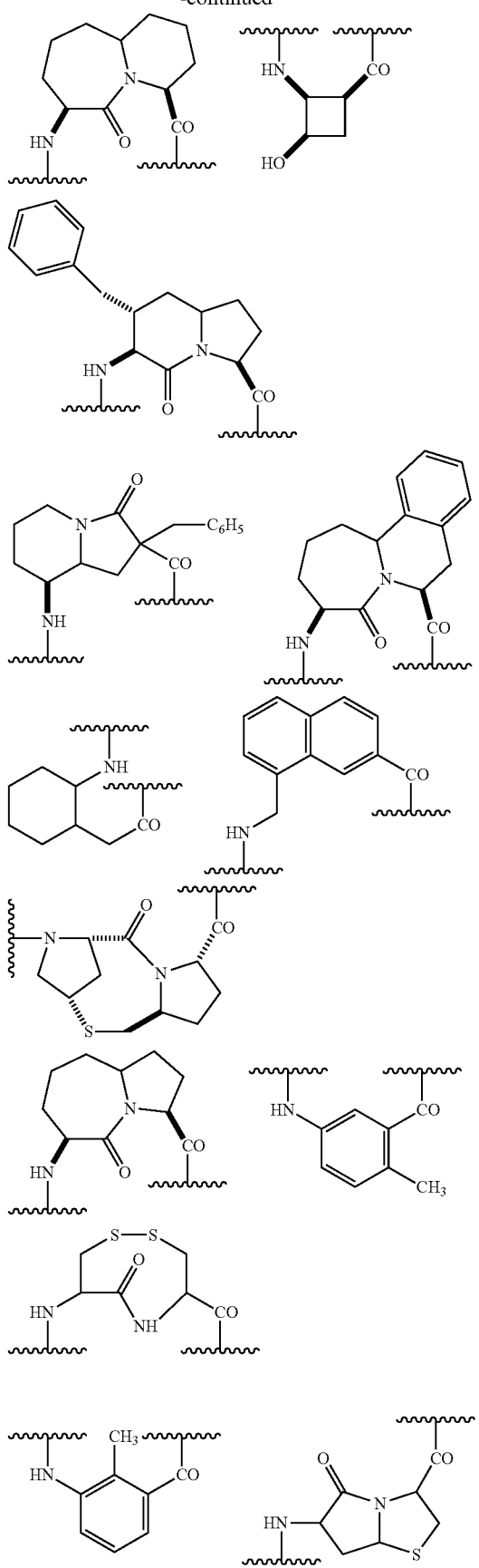

-continued

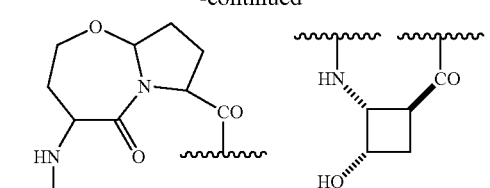

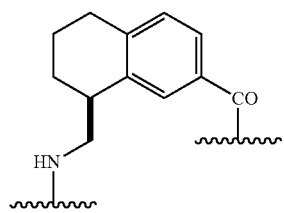

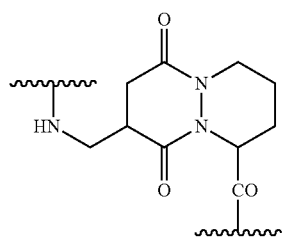

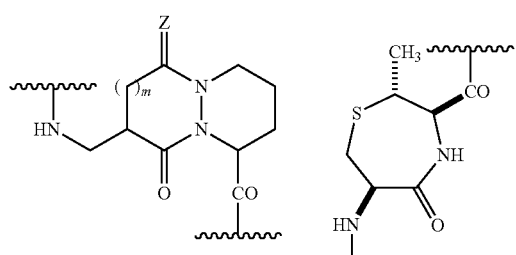

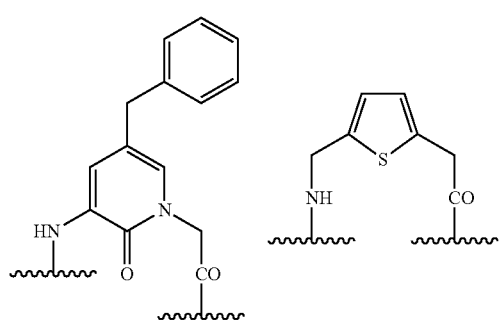

Z = H₂, m = 0, 1, 2, 3
Z = O, m = 0, 1, 2, 3

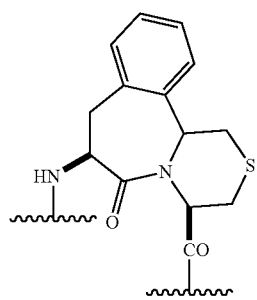

-continued

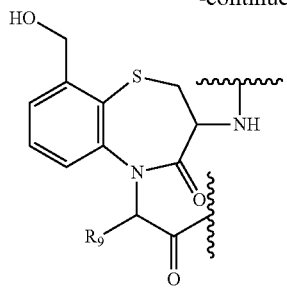

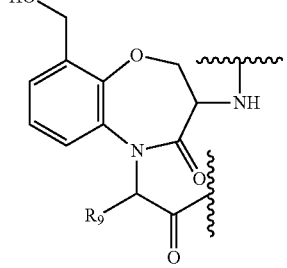

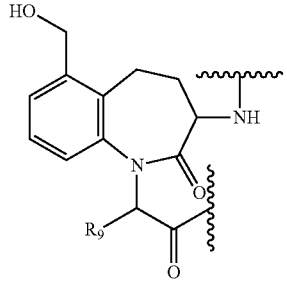

in which:

$R_2$ represents H, $C_1$-$C_6$ alkyl, nitrile, —NH—C(=NH)NH₂, —C(=NH)NH₂, —(CH₂)$_u$OH, —CO₂H, —CONH₂, F, CF₃, —(CH₂)$_v$NH₂, and/or —CONH(CH₂)$_w$NH₂, u, v and w being whole numbers comprised between 0 and 10.

$R_3$, and if appropriate $R_9$ and $R_{10}$, are selected independently of each other from the groups constituting the side chains of amino acids, for example H, CH₃—, (CH₃)₂CH—, CH₃—(CH₂)₃— or C₆H₅—CH₂—;

—$R_{11}$ represents H or a phenyl;

—$R_{12}$ represents H, CH₃—, C₂H₅— or C₆H₅—CH₂—;

m and the substituents X, Y and Z for each compound that contain them, are defined in a specific manner, and Me represents a methyl group.

In the above compounds comprising asymmetric centres, said asymmetric centres may be of configuration R or S.

Advantageously, the recurrent units —(NR₁—R-A-R'—CO)— of the oligomers (I) and (I') of the present invention are selected from the following groups:

(II)

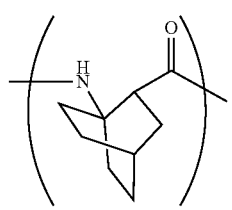

-continued

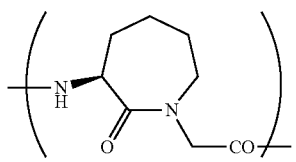
(III)

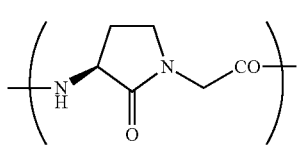
(IV)

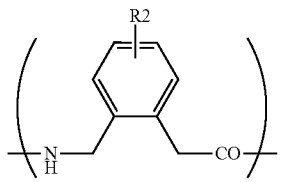
(V)

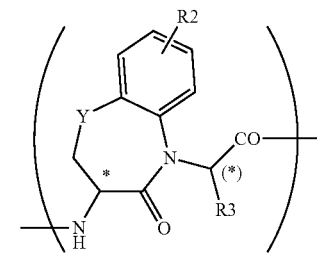
(VI)

R2 = H     R3 = side chain of amino acid
F
$(C_{1-6})$-alkyl     Y = O
OH     NH
CN     S
$C(=NH)NH_2$     $CH_2$
$NH-C(=NH)NH_2$
$CF_3$
$CONH_2$
$(CH_2)_u-OH$
$(CH_2)_v-NH_2$
$CO_2H$
$CO-NH-(CH_2)_w-NH_2$ In the formulas (I) or (I'), if n is too big, then it can undergo problems of synthesis and/or solubility. If n is too small, the oligomer does not enable the passage through a biological cell membrane.

Advantageously, for the formulas (I) and (I'), n is comprised between 2 and 10 and even more advantageously, n is comprised between 4 and 8.

Advantageously, the oligomers of formulas (I) and (I') may be heterooligomers, in other words comprising at least two different types of recurrent units.

Advantageously, the oligomer (I) or (I') of the present invention is a heterooligomer or $-(NR_1-R-A-R'-CO)_n-$ has the formula (VII):

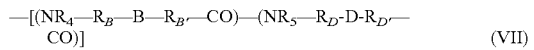
(VII)

in which:
the recurrent units $(NR_5-R_D-D-R_{D'}-CO)$, represent constrained dipeptide or tripeptide mimics, advantageously beta turn inducers;
the recurrent units $-(NR_4-R_B-B-R_{B'}-CO)-$ and $-(NR_5-R_D-D-R_{D'}-CO)-$ are different from each other;

$R_B$, $R_D$, $R_{B'}$ and $R_{D'}$ independently of each other, represent a bond or a $C_1$-$C_6$ alkyl group optionally substituted by an aryl group or by a side chain of an amino acid;

B represents a hydrocarbon cycle or a heterocycle, monocyclic or polycyclic, saturated or unsaturated, comprising one or more cycles of 3 to 10 atoms each and a total number of cycles not exceeding 3, optionally substituted by one or more groups selected from the group constituted of $C_1$-$C_6$ alkyl, oxo (=O), nitrile, $-C(=NH)NH_2$, $-NH-C(=NH)NH_2$, $-(CH_2)_uOH$, $-CO_2H$, $-CONH_2$, F, $CF_3$, $-(CH_2)_vNH_2$, and/or $-CONH(CH_2)_wNH_2$, u, v and w being whole numbers comprised between 0 and 10.

D represents a hydrocarbon cycle or a heterocycle, monocyclic or polycyclic, saturated or unsaturated, comprising one or more cycles of 3 to 10 atoms each and a total number of cycles not exceeding 3, optionally substituted by one or more groups selected from the group constituted of $C_1$-$C_6$ alkyl, oxo (=O), nitrile, $-C(=NH)NH_2$, $-NH-C(=NH)NH_2$, $-(CH_2)_uOH$, $-CO_2H$, $-CONH_2$, F, $CF_3$, $-(CH_2)_vNH_2$, and/or $-CONH(CH_2)_wNH_2$, u, v and w being whole numbers comprised between 0 and 10;

$R_4$ represents a hydrogen atom or instead $R_4$ forms a cycle with the nitrogen atom to which it is bonded, said cycle being either condensed with the group B, or bonded to the group B by a $C_1$-$C_6$ alkyl bond or bonded to B by a spiro junction;

$R_5$ independently of $R_4$, represents a hydrogen atom or instead $R_5$ forms a cycle with the nitrogen atom to which it is bonded, said cycle being either condensed with the group D, or bonded to the group D by a $C_1$-$C_6$ alkyl bond, or bonded to D by a spiro junction.

Advantageously, the two units $-(NR_4-R_B-B-R_{B'}-CO)-$ and $-(NR_6-R_D-D-R_{D'}-CO)-$ are units of formula (VI) different to each other.

Advantageously, one of said derivatives of formula (VI) is a compound of formula (VIII):

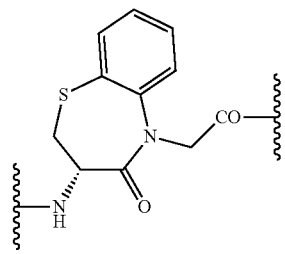 [SMILES: *N[C@@H]1CSc2ccccc2N(CC(*)=O)C1=O]

Advantageously, in the oligomers (I) and (I'), the spacer groups $X_1$ and $X_2$, independently of each other are a bond or selected from the following groups:

$-NH-(CH_2CH_2O)_2CH_2CO-$     (IX)

$-NH-(CH_2)_5CO-$     (X)

The active ingredient (AI) is a molecule known for its biological action, in particular used in human medical therapy. The active ingredient may also be used for the diagnosis of diseases. The active ingredient may be of natural or synthetic origin. The active ingredient may be peptidic. The active ingredient may be proteic. Generally speaking, the subject of the present invention makes it possible to facilitate the passage through the cell membrane of an active ingredient requiring such transport. Said cell membrane may be at the level of tissues targeted by the active ingredient whatever the mode of administration, and/or at the level of the digestive tract (in the case of an administration by oral route), and/or at the level of a pathogen (bacteria, parasite, fungus). Advantageously, the active ingredient is selected from the group of medicines treating for example lysosomal diseases, for example Gaucher disease, cancer, diseases associated with cell proliferation and differentiation, diseases associated with the metabolism, diseases of genetic or viral origin, infectious or allergic diseases, haematopoietic diseases, immune diseases, cardiovascular diseases, neurological diseases, for example Alzheimer's disease, haematological diseases. For example the active ingredient may be: an antiacne, an antiallergy, an anxiolytic, an antiasthmatic, an anticancer, an lipopenic, a hormonal contraceptive, an antidepression, an antidiabetes, an antalgic, an antiasthenic, a antihypertension, an antifungicide, an antibiotic, a sleep inducer, a hormone, an antimigraine, a medicine for overweight, an antiparkinsonian, a neuroleptic, a non steroid or steroid anti-inflammatory, an ovulation inducer, a bronchial fluidifier, an anticough, an erection inducer, an antiulcer agent.

Advantageously, the active ingredient is selected from the group of medicines treating lysosomal diseases, for example Gaucher, Fabry and Pompe disease; the group of medicines treating cancer or Alzheimer's disease.

Advantageously, the active ingredients of the oligomer of formula (I) are selected from the group of medicines, siRNA, miRNA, or peptides and even more advantageously, they are selected from the group of medicines for the treatment of lysosomal diseases, cancer, or Alzheimer's disease.

$R_6$ and/or $R_7$ may be one or more markers in order to trace the oligomer.

Said markers may be biotinyl markers, coloured markers, fluorescent markers, markers with metal complexes such as silver complexes, markers for electrophoresis in particular 2D, markers of RNA or tRNA in other words complexing with RNA or tRNA, markers detectable in UV-VIS, markers with encapsulated xenon or for encapsulating xenon, markers for any medical imaging technique, and their kind.

Advantageously, the marker is selected from the following compounds: fluorescein, sodium salt of fluorescein, 4',5'-Bis [N,N-bis(carboxymethyl)-5 amino methyl]fluorescein, 6-[fluorescein-5(6)-carboxamido]hexanoic acid, 6-[fluorescein-5 (6)-carboxamido]hexanoic acid ester N-hydroxysuccinimide of fluorescein-5(6)-isothiocyanate, fluorescein-α-D-N-acetylneuraminide-polyacryl-amide, fluorescein amidite, fluorescein-di(β-D-galactopyranoside), fluorescein-di-(β-D-glucopyranoside), fluorescein diacetate, fluorescein-5(6)-isothiocyanate diacetate, fluorescein-5-maleimide diacetate, fluorescein-6-isothiocyanate diacetate, fluorescein dibutyrate, fluorescein dilaurate, diphosphate salt of triammonium fluorescein, fluorescein hyaluronic acid, fluorescein isothiocyanate-Dextran 500000-Conjugate, isomer I of fluorescein isothiocyanate, fluorescein-dextran isothiocyanate, mercury-fluorescein acetate, mono-p-guanidinobenzoate-fluorosuccinic hydrochlorate, fluorescein O,O'-diacrylate hydrochlorate, fluorescein O,O'-dimethacrylate, fluorescein o-acrylate, fluorescein O-methacrylate, N-hydroxysuccinimide fluorescein ester, fluorescein-5-thiosemicarbazide, fluorescein-α-D-galactosamine polyacrylamide, fluorescein-α-D-mannopyranoside-polyacrylamide, 4(5)-(iodoacetamido)-fluorescein, 5-(Bromomethyl)fluorescein, 5-(Iodoacetamido) fluorescein, diacetate of the ester of N-succinimidyl-5-Carboxy-fluorescein, diacetate of the ester of N-succinimidyl-6-carboxy-fluorescein, aminophenyl-fluorescein, Biotin-4-fluorescein, hydroxyphenyl-fluorescein, MTS-4-fluorescein, poly(fluorescein-isothiocyanate allylamine) hydrochlorate, poly(fluoresccine-O-acrylate), poly(fluorescein-O-methacrylate), PPHT-fluorescein acetate, 5-([4,6-dichlorotriazin-2-yl]amino)fluorescein hydrochlorate, 6-([4,6-dichlorotriazin-2-yl]amino)fluorescein hydrochlorate, poly[(methylmethacrylate)-co-(fluorescein-O-methacrylate)], poly[methylmethacrylate-co-(fluorescein O-acrylate)], 5(6)-(Biotinamidohexanoylamido) pentylthioureidylfluorescein, N-(5-fluoresceinyl)maleimide, disodium salt of Mercury-dibromo-fluorescein, fluorescein-di-[methylene-N-methylglycine], disodium salt of 2',4',5',7'-tetrakis-(acetoxymercuro)-fluoroscein, erythrosin B, ethyl eosin, 5-carboxy fluorescein, ester N-succinimidyl de 5-carboxy fluorescein ester perchlorate, rhodamine B octadecyl, N-hydroxysuccinimide ester of 6-Carboxy-fluorescein, dibenzyl fluorescein, rhodol, 6-amino fluorescein, rhodamine 6G, rhodamine B or rhodamine 123.

According to a preferred embodiment of the invention, in particular when the active ingredient is a protein, the active ingredient(s) may be substituted by one or more hydrophilic groups. Said hydrophilic groups may for example enable a better solubility of the vectorized active ingredient, or even the active ingredient alone. Said hydrophilic groups comprise at least one amino acid, preferably consisting of amino acids.

Advantageously, said hydrophilic groups comprise at least one acyl amino acid, preferentially acetyl.

Advantageously, said hydrophilic groups comprise amino acids and have an acylated terminal amine function, preferentially acetyl.

Advantageously, said hydrophilic groups consist of amino acids and have an acylated terminal amine function, preferentially acetyl. Advantageously, said hydrophilic groups comprise an amino acid and have an acylated terminal amine function, preferentially acetyl.

Advantageously, said hydrophilic groups comprise "Ac-D-Arg-O$_2$Oc-" in which Ac represents an acetyl group, D-Arg represents D-Arginine, O$_2$Oc represents 8-amino-3,6-dioxaoctanoyl.

Advantageously, said hydrophilic groups consist of "Ac-D-Arg-O$_2$Oc-" in which Ac represents an acetyl group, D-Arg represents D-Arginine, O$_2$Oc represents 8-amino-3,6-dioxaoctanoyl.

Advantageously, said hydrophilic groups comprise "Ac-D-Lys-O$_2$Oc-" in which Ac represents an acetyl group, D-Lys represents D-Lysine, O$_2$Oc represents 8-amino-3,6-dioxaoctanoyl.

Advantageously, said hydrophilic groups consist of "Ac-D-Lys-O$_2$Oc-" in which Ac represents an acetyl group, D-Lys represents D-Lysine, O$_2$Oc represents 8-amino-3,6-dioxaoctanoyl.

Such hydrophilic groups may include amino acids of the series L or the series D, natural or non natural. Advantageously, amino acids known to aid solubilization, such as arginine and/or lysine may be added. Advantageously, said amino acids are of the series D and the terminal amine of the hydrophilic group is substituted by an acyl group, in order that said hydrophilic groups are not easily hydrolysed in vivo.

Techniques for aiding the solubilization/solubility of active ingredients are well known to those skilled in the art.

Another subject of the present invention is a method of synthesis to obtain the oligomers of formulas (I) and (I').

The techniques used are similar to those used in peptide synthesis. One, several or all of the steps may be carried out in liquid phase.

One, several or all of the steps may be carried out on solid support.

An oligomer (I) or (I') is obtained by polymerisation of at least one constrained dipeptide or tripeptide mimic amino acid, which can be a β turn inducer, and which meets the formula:
NHR₁—R-A-R'—COOH   (XI)
in which the groups R₁, R, A and R' have the same signification as in the oligomer (I) or (I').
As examples of compounds, the compounds below, suitably protected, may be cited:
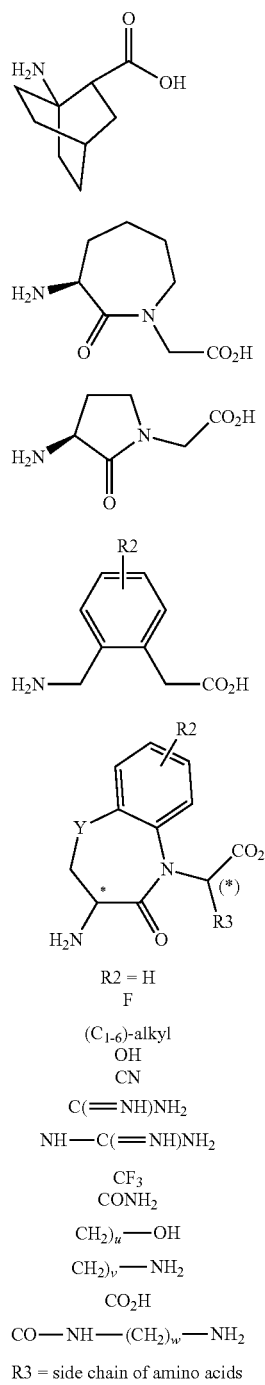
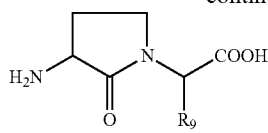
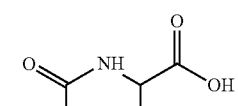
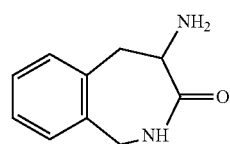
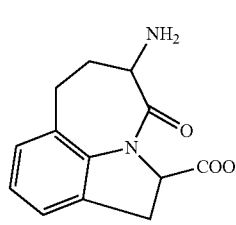
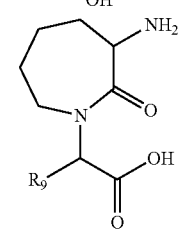
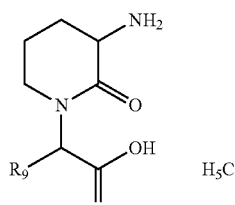
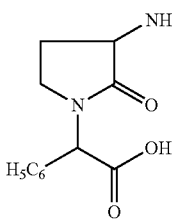
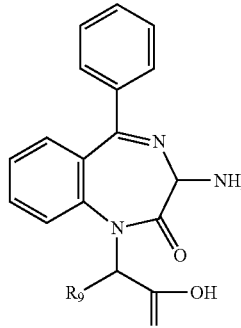
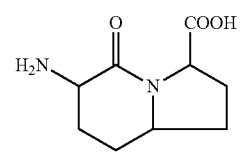
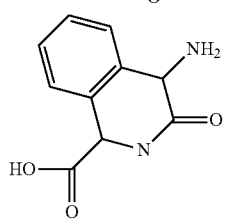
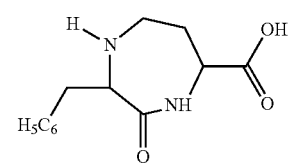
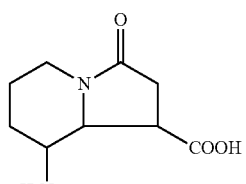
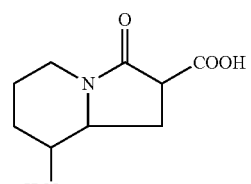
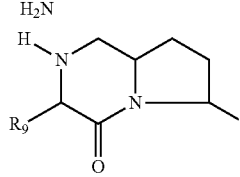

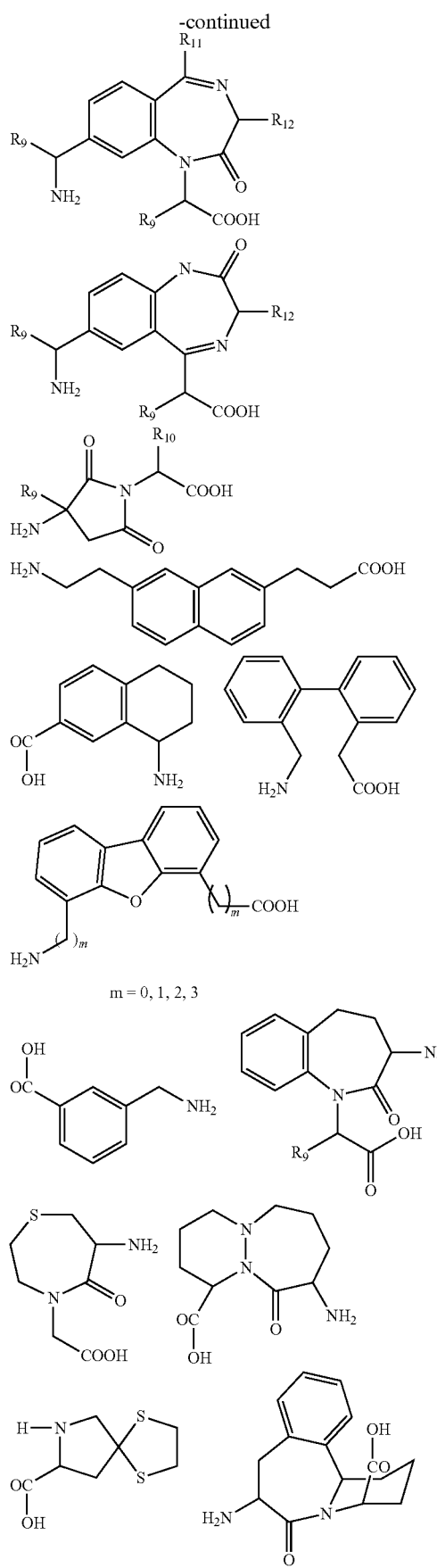
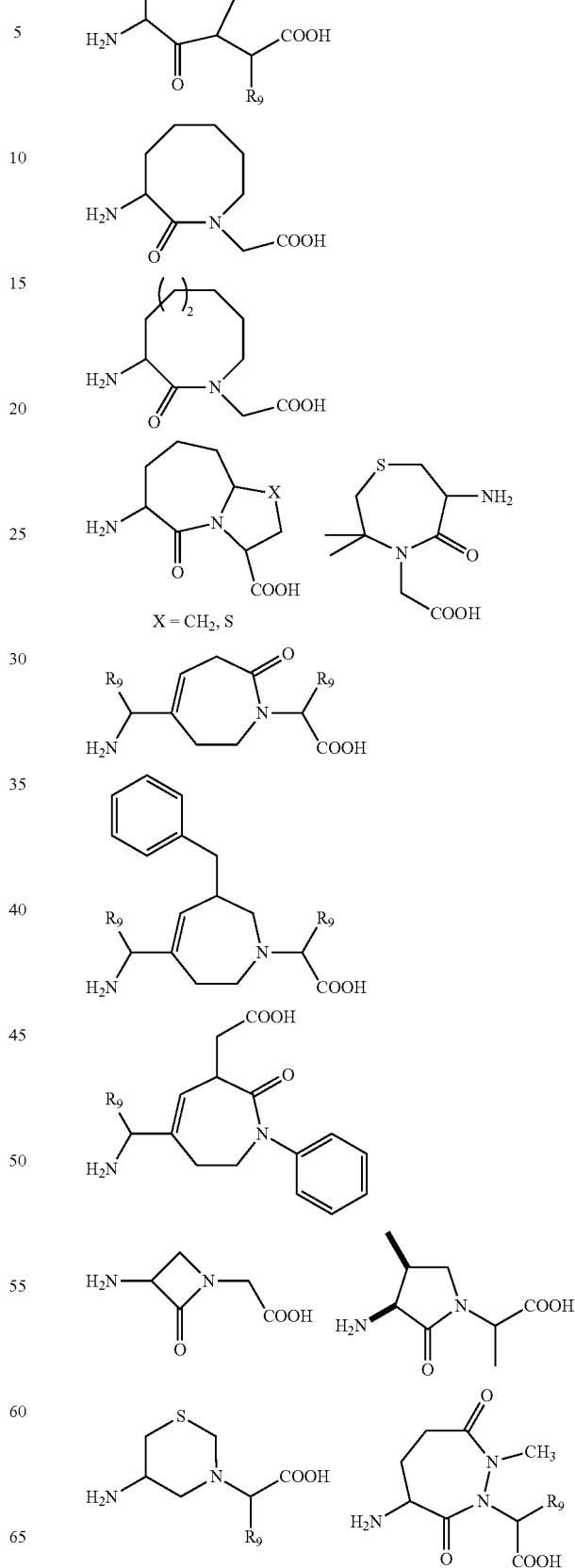
$X = CH_2, S$
$m = 0, 1, 2, 3$

-continued
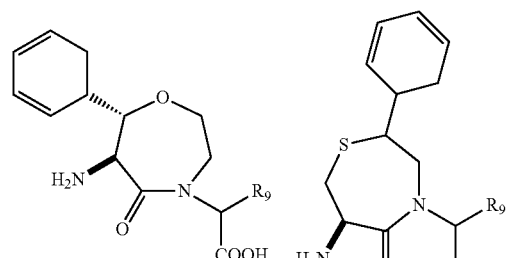
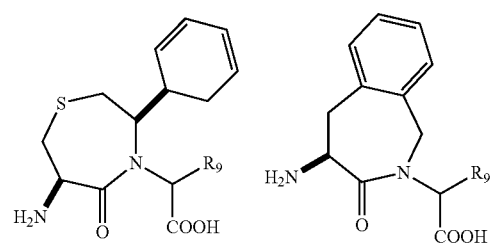
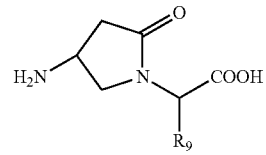
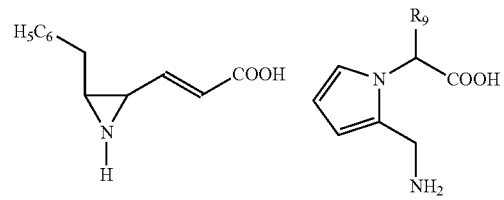
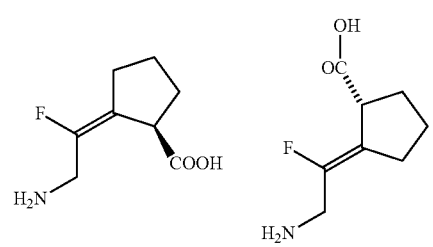
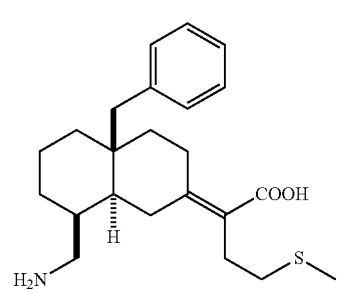
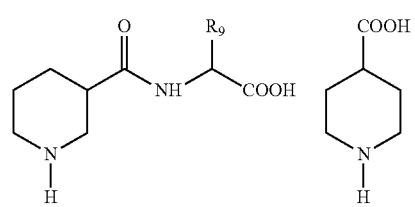
-continued
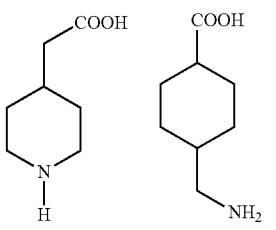
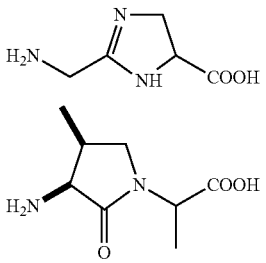
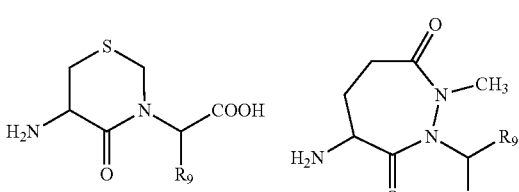
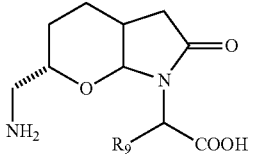
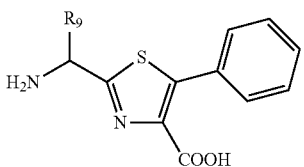
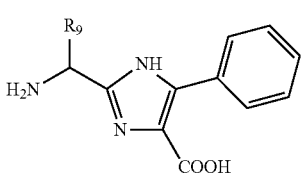
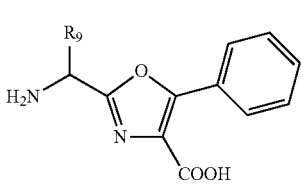
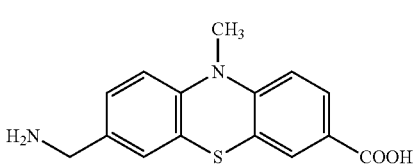

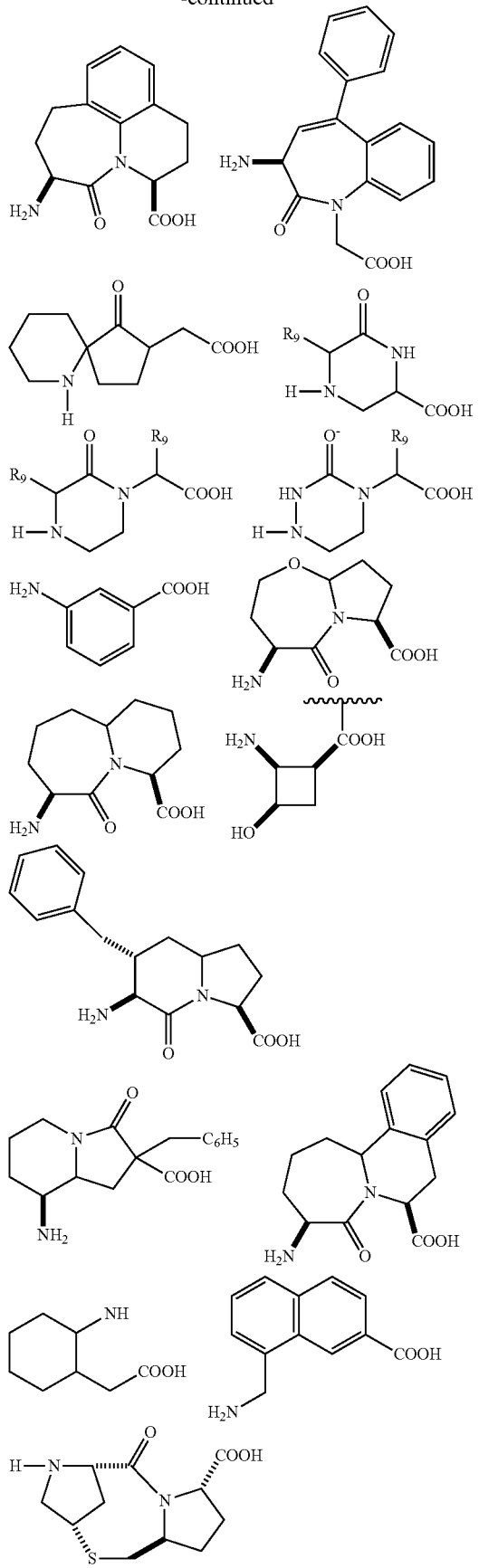
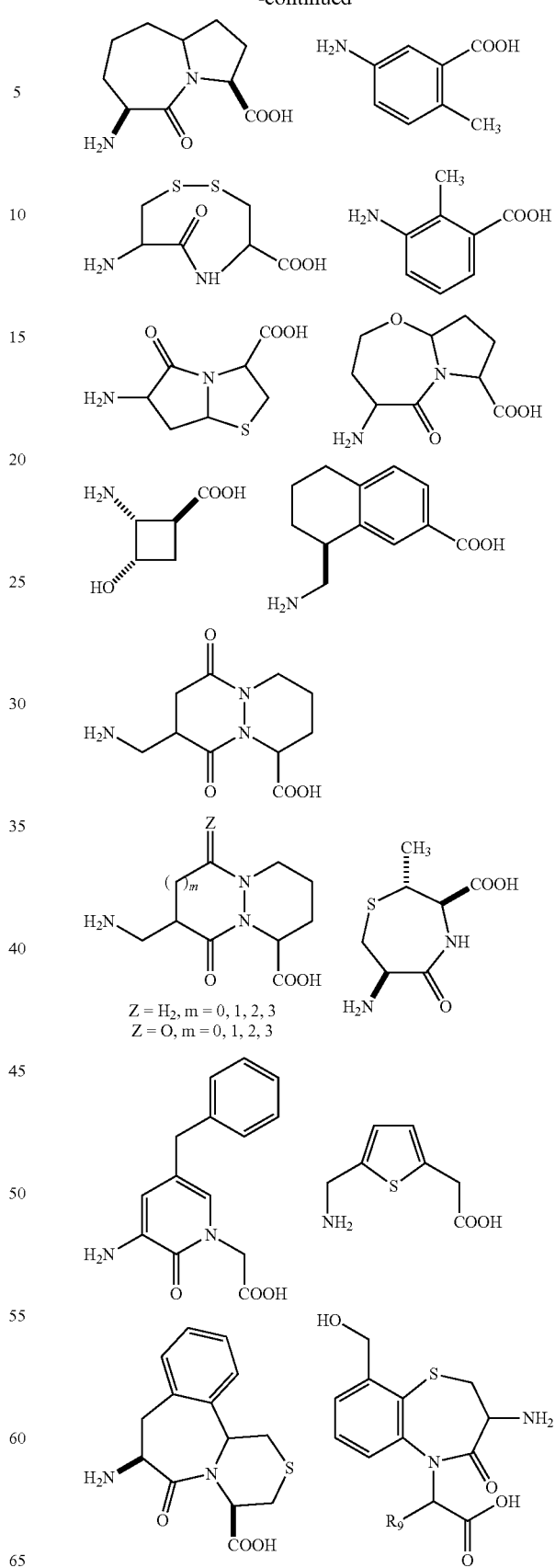
Z = H₂, m = 0, 1, 2, 3
Z = O, m = 0, 1, 2, 3

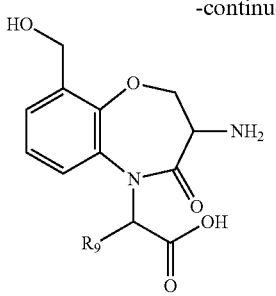

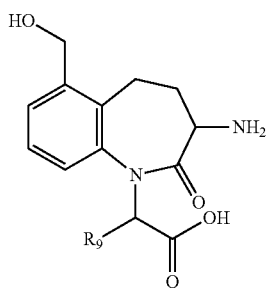

In the above compounds comprising asymmetric centres, said asymmetric centres may be of R or S configuration.

These monomers may be synthesised by methods described in the prior art. For example, Amblard, et al., J. Med. Chem., 1999, 42, 4193-4201, describe the synthesis of (3S) [amino]-5-(carbonylmethyl)-2,3-dihydro-1,5-benzothiazepin-4-(5H)-one and other monomers.

Advantageously the synthesis of the oligomer of formula (I) takes place in two major steps ($\alpha$) and ($\beta$): firstly ($\alpha$) by a polymerisation of recurrent units with or without $X_1$ and/or $X_2$ groups bonded to the recurrent N-terminal and/or C-terminal units, then in a second step ($\beta$) by bonding of the active ingredient onto the oligomer obtained. In the two steps, a selection of reactive chemical functions, such as certain hydroxyls, carboxylic acids, amines, etc., are protected by protector groups or techniques known to those skilled in the art, which may be found in: Greene, "Protective Groups in Organic Synthesis", Wiley, New York, 2007 4$^{th}$ edition; Harrison et al. "Compendium of Synthetic Organic Methods", Vol. 1 to 8 (J. Wiley & sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. E 22b, Vol. E 22c, Vol. E 22d., M. Goodmann Ed., Georg Thieme Verlag, 2002.

For the first step ($\alpha$), in an identical manner to conventional peptide synthesis, a direction of synthesis may be given. In the structures given above, an amide bond may be formed between two recurrent units to form an oligomer, by the use of a coupling agent. The recurrent units each having a COOH end and an $NH_2$ end, protected or not, before reaction, the part remaining non reactive (thus protected) is referred to as C-terminal or N-terminal end respectively. Thus a direction of synthesis may be defined depending on the end by which those skilled in the art wish to enlarge the oligomer: C→N or N→C syntheses.

Example of structure that can be produced by the present method:

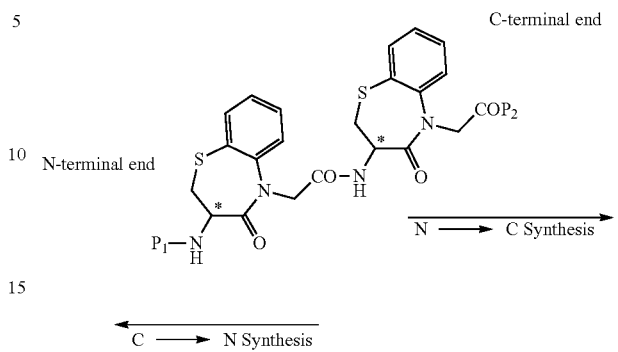

$P_1$ group N-protector or H
$P_2$ group C-protector or OH or $NH_2$

Then, one of the protector groups $P_1$ or $P_2$ is cleaved by techniques known to those skilled in the art and a second coupling reaction may be carried out. The controlled polymerisation of recurrent units is thereby obtained by successive steps of coupling/de-protection making it possible to obtain an oligomer of desired size and in an unequivocal manner. The final oligomer may be de-protected in fine either selectively on the carboxylic function, or on the amine function, or totally.

Thus in the present case, in step (a), whether in liquid phase or in solid phase, the synthesis can take place in the direction C→N or N→C. The direction of the synthesis may be dictated by the desired final molecule or by other synthesis factors, such as risks of epimerisation. Whatever the direction of the synthesis, those skilled in the art know the strategies (there are several of them) to incorporate the active ingredient (AI) not just at the N-terminal level on $X_1$ but also on the C-terminal level on $X_2$. The final molecule is totally or partially de-protected according to techniques known to those skilled in the art.

Advantageously, an oligomer (I) or (I') is obtained by a method of polymerisation in solid phase, according to a conventional peptide synthesis strategy on support: a resin bearing an amine function is condensed with an amino acid protected on its amine function, then the fragment thereby fixed on the resin is lengthened from the C-terminal side to the N-terminal side, before being separated from the resin.

In the method of polymerisation in solid phase, each step of coupling of a compound (XI) protected beforehand on its amine function (XI') comprises the actual coupling reaction in the presence of a coupling agent, the washing of the product obtained after the coupling, then the de-protection of the amino group of the fixed —$NR_1$—R-A-R'—CO— unit.

Advantageously, the method of preparation of the oligomer of formula (I) takes place by the following successive steps:
a) polymerisation by a strategy of peptide synthesis on solid support, comprising the reaction of the constrained dipeptide or tripeptide mimic unit, advantageously beta turn inducer, of following formula (XI'):

P—$NR_1$—R-A-R'—CO—OH (XI')

in which the group P is an N-protector group, the recurrent unit —N—$R_1$—R-A-R'—CO— and the terms A, R, R' and $R_1$ are as defined above for the formula (I') and the groups A, R, R' and $R_1$ suitably protected by protector groups, to synthesise the following product (XII):

H—($NR_1$—R-A-R'—CO)$_n$—$X_2$—$R_8$—(SS) (XII)

in which,
n and $X_2$ are as defined above;
$R_8$ is a precursor group of $R_7$ before cleavage, $R_7$ is as defined above;
(SS) is the solid support;
a2) optionally, if $X_1$ is not a bond, coupling reaction between P—$X_1$—OH, in which the group P is a N-protector group and $X_1$ is as defined above, and the N-terminal amine of the product (XII), followed by a step of de-protection of the N-terminal end to synthesise the following product (XII'):

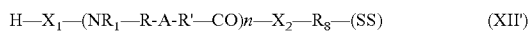

H—$X_1$—(N$R_1$—R-A-R'—CO)n—$X_2$—$R_8$—(SS)     (XII')

c) coupling reaction between an active ingredient (AI) and the N-terminal amine of the product (XII'), to synthesize the following product (XIII):

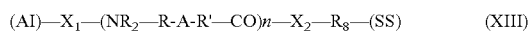

(AI)—$X_1$—(N$R_2$—R-A-R'—CO)n—$X_2$—$R_8$—(SS)     (XIII)

in which,
(AI) is as defined above,
d) a cleavage reaction making it possible to free the oligomer of formula (I) from the solid support from the product of formula (XIII).

Within the scope of the present invention, the terms solid supports, resins supports or resins are equivalent.

Advantageously, the method comprises a step (a1) prior to a step (a) of coupling of a spacer group $X_2$ on the solid support For step (a), any resin used in a conventional manner in peptide syntheses may be used as resin support. As an example, a 4-methylbenzhydrylamine resin (hereafter designated MBHA resin), or a resin known as Merrifield, which is a copolymer of styrene and divinylbenzene functionalised by chlorobenzyl may be cited. The two resins are commercially available resins distributed particularly by the firms Novabiochem and Bachem. The resins PAL-PEG-PS, which are copolymers of 5-(4-aminomethyl-3,5-dimethoxyphenoxy) valeric acid-polyethylene glycol-polystyrene may also be cited.

"Rink amide" type resins (4-[2',4'-dimethoxyphenyl-(9-fluorenylmethyloxycarbonyl)aminomethyl]phenoxy-aminomethyl polystyrene) and "Wang" (4-benzyloxy-benzyl polystyrene alcohol) may also be used as solid support (SS).

Advantageously the resins used are of "Wang" or "Rink Amide" type. The coupling agent may be selected from the coupling agents conventionally used in peptide synthesis. The following may be cited for example: N,N'-dicyclohexylcarbodiimide (DCC), 1-ethyl-3-(3'-dimethylaminopropyl)-5 carbodiimide hydrochloride (EDC), O-(1H-benzotriazol-1-yl)-N,N,N',N'-tetramethyluronium tetrafluoroborate (TBTU), benzotriazol-1-yl-oxytris(dimethylamino)phosphonium hexafluorophosphate (BOP), O-(7-azabenzotriazol-1-yl)-1,2,3-tetramethyluronium hexafluorophosphate (HATU), O-benzotriazol-1-yl-N,N,N',N'-tetramethyluronium hexafluorophosphate (HBTU), N-hydroxy-5-norbornene-2,3-dicarbodiimide, or any other coupling agent in a solvent such as ether, acetone, chloroform, dichloromethane, ethyl acetate, dimethylformamide (DMF), tetrahydrofuran (THF), acetonitrile, dimethylsulphoxide (DMSO), N-methyl pyrrolidone (NMP), cooled or at ambient temperature, preferentially in the presence of an acylation catalyst such as N-hydroxybenzotriazole (HOBt), 1-hydroxy-7-azabenzotriazole (HOAt), N-hydroxysuccinimide and their kind.

Symmetric anhydrides preformed from a monomer (XI') and DCC may also be used for the coupling.

The washing of the products obtained after each coupling phase may be carried out by means of solvents used conventionally in solid phase peptide syntheses.

As an example, dimethylformamide (DMF), methanol and dichloromethane (DCM) may be cited.

The reagent used for the de-protection of the amine group after a coupling step depends on the protection agent used. For example, if the protection is carried out by a Boc group, the de-protection is carried out advantageously by means of a solution of trifluoroacetic acid (TFA). If the protection is carried out by a Fmoc group, the de-protection may be carried out by piperidine. Generally speaking, the protector groups and the de-protection agents used in a known manner during solid phase peptide syntheses may be used during the synthesis of the oligomers of the present invention.

The oligomer may advantageously be separated from the resin by treatment by an acid. As an example, trifluoroacetic acid in the presence of tris-isopropylsilane and water or hydrofluoric acid in the presence of anisole may be cited, according to the type of resin used. In these conditions, the protection of the terminal amino group before separation of the resin may be carried out by a stable urethane group in acid conditions of cleavage or by a stable acyl group in the same conditions. When the separation is carried out by trifluoroacetic acid, the amino group is protected for example by a Fmoc or Boc group defined previously.

The preparation of the oligomers in solid phase is carried out in an advantageous manner in an automatic synthesizer used in a conventional manner for the synthesis of peptides on solid support. In this type of apparatus, the succession of the different operations of coupling, washing, de-protection is computer controlled.

FIGURE CAPTIONS

FIG. 1 describes the internalisation of oligomers in human cancerous mammary cells of the line MDA-MB-231. FIG. 1A describes the intensity of the fluorescence emitted by the oligomers marked by the fluorescein. FIG. 1B describes the intensity of the fluorescence of JMV 3229 as a function of temperature. FIG. 1C describes the intensity of the fluorescence as a function of the concentration of oligomers. FIG. 1D describes the evolution of the fluorescence as a function of time (kinetic).

Figure 2:
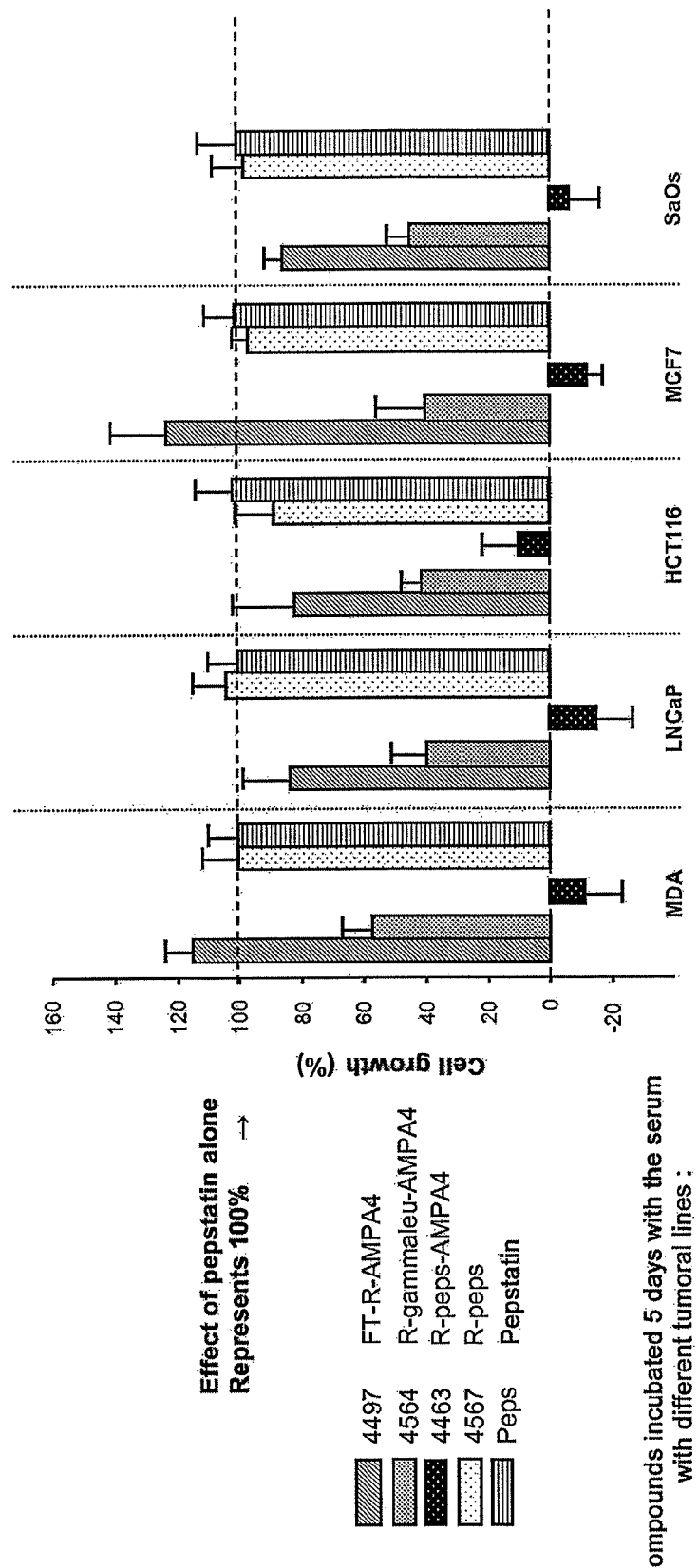

FIG. 2 describes the cell growth (in percentage of number of cells with respect to a pepstatin control) of cancerous cells (mammary MDA-25 MB-231 and MCF7, prostatics LNCaP, colic HCT116, osteoblastics $SaOs_2$) as a function of their incubation for 5 days with 1 oligomer of AMPA (4497), pepstatin alone (Peps), [$Val^1$]-Pepstatin bonded to arginine (4567) and two conjugate inhibitors of cathepsin D-oligomer of AMPA bonded to an arginine residue (4564 and 4463). The negative percentages correspond to a reduction in the number of cells with respect to the initial cellular seeding.

Figure 3:
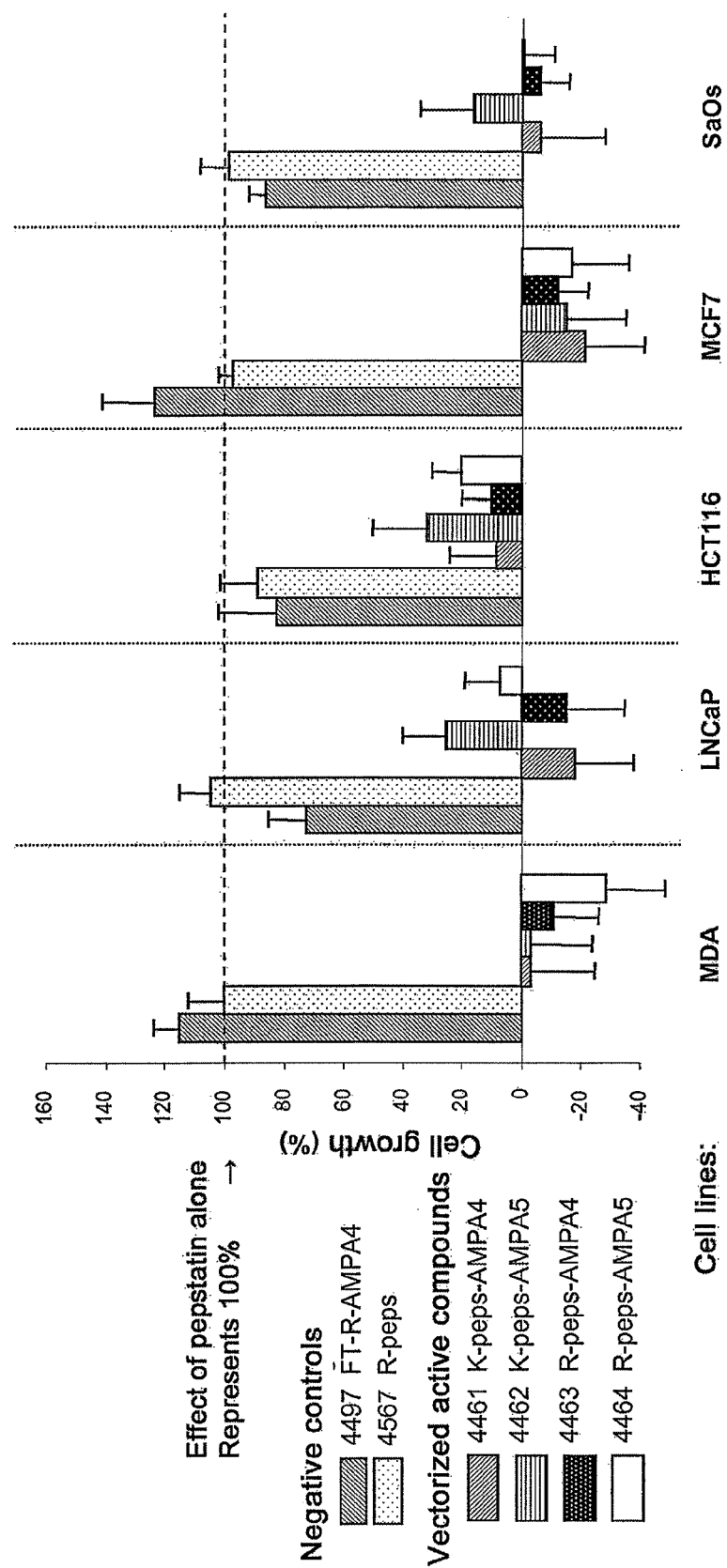

FIG. 3 describes the cell growth (in percentage of number of cells with respect to a pepstatin control) of cancerous cells (MDA-MB-231, MCF7, LNCaP, HCT116, $SaOs_2$) as a function of their incubation for 5 days with 1 oligomer of AMPA (4497), [$Val^1$]-Pepstatin bonded to conjugated arginine 5 (4567) and 4 [$Val^1$]-Pepstatin-oligomer of AMPA bonded to a lysine or arginine residue (4461, 4562, 4463, 4564). The negative percentages correspond to a reduction in the number of cells with respect to the initial cellular seeding.

FT represents carboxyfluorescein which makes it possible to control the penetration by fluorescence measurement.

The present invention is described in greater detail using the following examples, which are given by way of illustration and to which the invention is not limited.

Example 1

Synthesized Oligomers

Oligomers of different sizes have been synthesized. These oligomers may be of hydrophobic, hydrophilic or amphipatic nature as a function of the mimics used. They have the ability to pass through the cell membranes and are probably internalised by endosomal route. In order to monitor the internalisation of the oligomers in the cells by fluorescence microscopy, fluorescein isothiocyanate has been used. The fluorescent probe (fluorescein) is introduced, either directly on the N-terminal end of the poly-CM (CM=constrained mimic) anchored to the resin (compounds 1 to 3 and 7) or on the amine function of a spacer (compounds 4-6 and 8-9). The importance of the configuration has been evaluated by the preparation of derivatives of DBT (compounds 1-6) and of LBT (compounds 7-9).

Synthesis schema 1: Synthesis of oligo-(DBT) and oligo-(LBT) marked by fluorescein

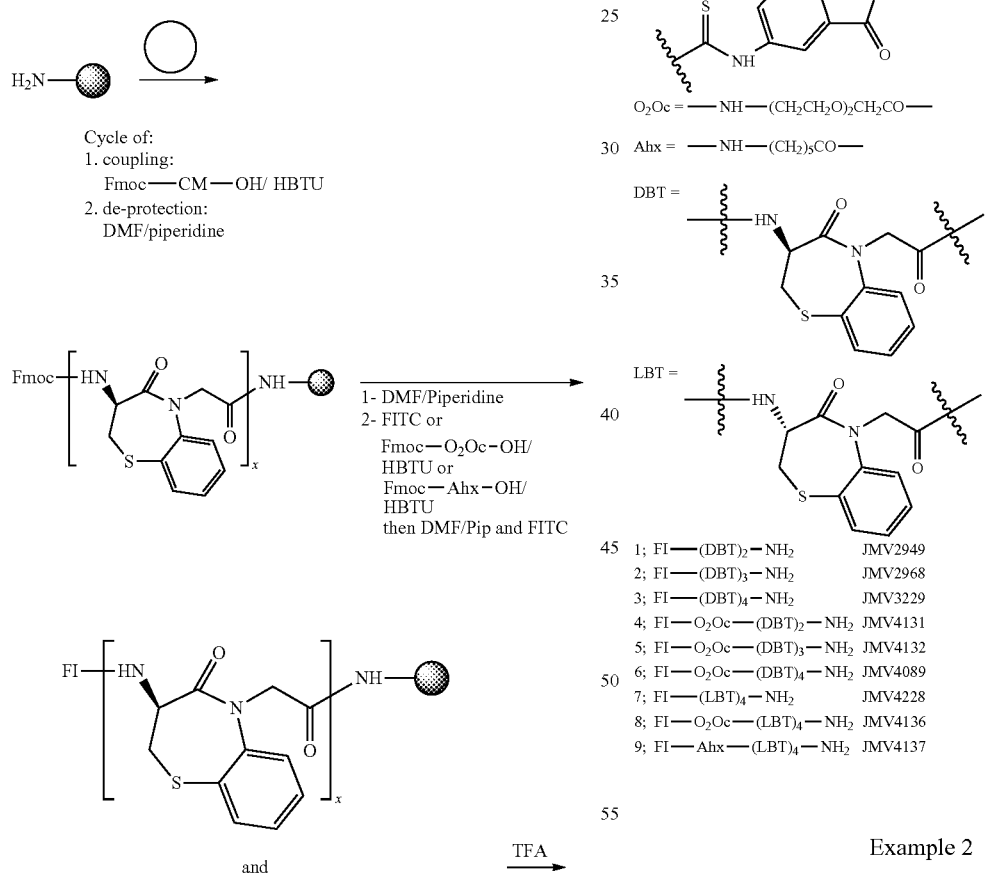

1; Fl—(DBT)$_2$—NH$_2$    JMV2949
2; Fl—(DBT)$_3$—NH$_2$    JMV2968
3; Fl—(DBT)$_4$—NH$_2$    JMV3229
4; Fl—O$_2$Oc—(DBT)$_2$—NH$_2$  JMV4131
5; Fl—O$_2$Oc—(DBT)$_3$—NH$_2$  JMV4132
6; Fl—O$_2$Oc—(DBT)$_4$—NH$_2$  JMV4089
7; Fl—(LBT)$_4$—NH$_2$    JMV4228
8; Fl—O$_2$Oc—(LBT)$_4$—NH$_2$  JMV4136
9; Fl—Ahx—(LBT)$_4$—NH$_2$  JMV4137

Example 2

Biological Evaluation

First of all, the oligomers bearing the fluorescent probe are tested for their ability to penetrate into the cells (MDA-MB-231 breast cancer lines). Typically, two experiments are carried out: measurements of the total fluorescence by fluorimetry after arranged trypsinisation and lysis of the cells, and by confocal fluorescence microscopy with specific markers of cellular organites.

Tetraoligomers of DBT are capable of internalising themselves in cells with the same efficiency as octa-arginine (R8) described by Wender's group (Standford, USA) and which forms part of the reference CPP described to date in the literature. Specific markers make it possible to demonstrate that these compounds are internalised by endosomal route and are localised after 16 hours in lysosomes. This specific localisation has a certain interest for targeting certain pathologies: lysosomal diseases, Alzheimer's disease, certain cancers.

Firstly, the quantity absorbed and the internalised fraction of the oligomers have been analysed (FIG. 1A). For this reason, cells of the line MDA-MB-231 of breast cancer have been incubated in a medium containing $10^{-5}$ M of compounds (1-6 of schema 1) marked by fluorescence, for 3 hours. Octa-arginine marked by fluorescein has been used as positive control, and carboxyfluorescein as negative control. After incubation of the oligomers of DBT, the cells have been washed with a phosphate buffer. To determine the internalised fractions of the compounds, a treatment of 5 minutes with trypsin has been carried out in order to eliminate the compounds remaining bonded to the cellular membranes during the transduction. The emission of fluorescence has been measured on a microplate reader.

As is shown in FIG. 1A, the quantities of internalised oligomers are important and correspond at least to 40% of all of the oligomers retained on the cells. The greatest intensity of fluorescence observed is for the compound $DBT_4$ (JMV3229), the intensity of fluorescence of the oligomers $DBT_3$ (JMV2968) and $DBT_2$ (JMV2949) being considerably lower. The latter have internalisation capacities at least 8 times less than that of derivatives of $DBT_4$. The cellular absorption appears dependent on the length of the oligomer with an emission of fluorescence increasing with the size of the oligomer. Moreover, the derivatives of $DBT_4$ are as efficient as octa-arginine despite that fact that the $DBT_4$ are not charged. A better efficiency of $DBT_4$ with respect to shorter oligomers may be associated with an increase in the hydrophobicity and/or a progressive structuring of the oligomer. The compounds JMV4137 and JMV4228 constructed by polymerisation of the monomer L-benzothiazepinone (LBT) are as efficient as their D counterparts, indicating that the configuration of the DBT fragment is not important.

This result should exclude the involvement of a receptor-dependent mechanism for the cellular internalisation of $DBT_4$. The introduction of a spacer at the N-terminal end of the oligomers (compounds JMV4089, JMV4136 and JMV 4137) does not induce any significant perturbation of the system.

Example 3

Analysis of the Temperature Factor

An analyse of the dependence of the internalisation vis-à-vis temperature has been carried out by incubating cells with $10^{-5}$ M of JMV3229 at 4° C. and 37° C. (FIG. 1B). The cellular absorption is reduced by three at low temperature suggesting an energy dependent endocytotic passage, rather than a passive penetration of the oligomer in the cell.

Example 4

Dose-Response Analysis

A dose-response analysis has been carried out to compare the absorption of oligomers of DBT vis-à-vis octa-arginine $R_8$ (FIG. 1C). The penetration of all the compounds appears to be dose-dependent.

Example 5

Kinetic Study

The kinetic study carried out with the most efficient DBT, JMV 3229, (FIG. 1D) shows that its cellular entry is as rapid as that of octa-arginine $R_8$, but no plateau is observed after 3 hours. In contrast, the internalisation of JMV3229 increases up to 16 hours to reach a concentration 11 times greater than that of octa-arginine $R_8$.

Example 6

Cytotoxicity Analysis

The cytotoxicity of this novel class of molecules has also been determined in cells of the line MDA-MB-231 by using a cellular viability diagnostic test, MTT. After an incubation of 5 days, the compounds at the concentrations used for internalisation studies do not show any significant effect on cellular viability, except for the compound JMV4131 at $10^{-5}$M. These results indicate that poly-DBT does not exhibit any risk of specific cyclotoxic effects, which is favourable for their use as vectors for the delivery of medicine.

Example 7

CLSM Analysis

Confocal laser scanner microscopy (CLSM) analysis has also been carried out on living cells to determine the intracellular internalisation and distribution. This experiment has been associated with a kinetic study of the internalisation of oligomers of DBT.

The co-coloration with a membrane marker (marking of lipid rafts) has been carried out to check that the hydrophobic compound JMV3229 has not been trapped in the membrane. It has been observed by CLSM analysis and in agreement with the results of FIG. 1D that the internalisation of this compound in the cellular organites increased up to 16 hours then decreased. In addition, the results show that non-cationic JMV3229 has an internalisation comparable to that of octa-arginine $R_8$ after 3 hours.

The internalisation and the localisation of the oligomers of LBT, JMV4137 and JMV4089 are similar to those of the compound JMV3229.

In order to have a better idea of the mechanism of translocation of the oligomers DBT, co-colorations have been made with various fluorescents markers for sub-cellular components, such as the nucleus, the plasmatic membrane and the lysosomes. The results show that JMV3229 is localised in non marked vesicules (endosomal) after 3 hours and become essentially co-localised with a lysosomal marker after 16 hours.

Similar results have been obtained with the oligomers JMV4089 and JMV4137. The effect of temperature on the internalisation of the compound JMV3229 has been determined. At 4° C. the majority of the compound JMV3229 is co-localised with the membrane marker rather than internalised. This confirms the results shown in FIG. 1B and suggests an energy-dependent internalisation mechanism.

In conclusion, these results indicate the potential of these oligomers in the targeting of the endolysosomal compartment. Although lysosomal addressing has the drawback of a possible degradation of the active ingredient by lysosomal enzymes, recent studies show an interesting clinical usefulness in targeting a therapy towards said compartment. In conclusion the proven efficiency of the cellular penetration of short oligomers of D- or L-BT, offer a new class of vectors having the particularity of being non-cationic transporters.

Example 8

Vector-Drug Bio-Conjugates

We have shown that the tetra-oligomers of DBT are capable of entering into the cells with the same efficiency as octa-arginine ($R_8$), one of the best CPP described in the literature. These compounds are internalised by endosomal route and are localised after 16 hours in the lysosomes. This specific localisation has a certain interest to target certain pathologies such as lysosomal diseases, Alzheimer's disease and certain cancers. These original and non toxic compounds have the particularity of being non cationic, which may be an advantage for the vectorization of active molecules targeting the central nervous system.

The application of these vectors within the context of a tumoral pathology is now explored. We are interested in particular in certain cancers, particularly of the breast, in which cathepsin D, a protease of the endo-lysosomal system, is over-expressed and contributes to the proliferation of tumoral cells. We study the effect of a natural and powerful inhibitor of this enzyme, pepstatin A, on the proliferation of various tumoral cells. The inhibitor alone, on account of a too low intra-cellular penetration, is inactive. We have shown that bio-conjugates formed by inhibitors of cathepsin D (more specifically in our case described, the [Val$^1$]-pepstatin analogue of pepstatin or less active analogues such as the compound incorporating gammaleucine instead of statin) associated with constrained dipeptide mimic oligomers (more specifically in our case 2-aminomethyl-phenyl-acetic acid or AMPA) could penetrate into the cells, are localised preferentially in the endo-lysosomal system. In addition, said conjugates are capable of totally inhibiting at $10^{-5}$ M the proliferation of the tumoral lines tested (cf. FIGS. 2 and 3).

| JMV number | Chemical formula |
|---|---|
| 4463 | Ac-D-Arg-O$_2$Oc-([Val$^1$]-Pepstatin)-(AMPA)$_4$—NH$_2$ |
| 4461 | Ac-D-Lys-O$_2$Oc-([Val$^1$]-Pepstatin)-(AMPA)$_4$—NH$_2$ |
| 4462 | Ac-D-Lys-O$_2$Oc-([Val$^1$]-Pepstatin)-(AMPA)$_5$—NH$_2$ |
| 4464 | Ac-D-Arg-O$_2$Oc-([Val$^1$]-Pepstatin)-(AMPA)5- |
| 4567 | Ac-D-Arg-O$_2$Oc-([Val$^1$]-Pepstatin)-NH$_2$ |
| 4564 | Ac-D-Arg-O$_2$Oc-Val-Val-Val-yLeu-Ala-yLeu-(AMPA)$_4$—NH$_2$ |

[Val$^1$]-Pepstatin = Val-Val-Val-Sta-Ala-Sta- (with statin residue = Sta = (3S, 4S)-4-amino-3-hydroxy-6-methyl-heptanoyl
O$_2$Oc- = 8-amino-3,6-dioxaoctanoyl
GammaLeu = -Val-Val-Val-yLeu-Ala-yLeu- (with γLeu = (4S)4-amino-6-methyl-heptanoyl)

The construction of the compounds is:
"Hydrophilic residues (for problem of solubility, may be Arg, Lys, O$_2$Oc, or others)—Inhibitors—vectors" (example: Ac-D-Arg-O$_2$Oc-[Val$^1$]-Pepstatin-(AMPA)$_4$-NH$_2$).

The invention claimed is:
1. An oligomer represented by the generic formula (I):

$$R_6-X_1-(NR_1-R-A-R'-CO)_n-X_2-R_7 \quad (I)$$

said oligomer contains $R_6$ or $R_7$ or both,
in the case that $R_6$ or $R_7$ is present, at least one of $R_6$ or $R_7$ is an active ingredient (AI), optionally substituted active ingredient or a marker; in the case where $R_6$ is an active ingredient, which requires help through a cell membrane, or a marker, $R_7$ is selected from hydroxy, $C_1$-$C_6$ alkoxy, aryl-($C_1$-$C_6$)alkoxy)- groups, or NH$_2$ or $R_7$ represents an active ingredient, which requires help through a cell membrane, or a marker identical or different to $R_6$; in the case where $R_7$ is an active ingredient, which requires help through a cell membrane, or a marker, $R_6$ is selected from a hydrogen atom, a $C_1$-$C_6$ alkyl group, an aryl group-($C_1$-$C_6$ alkyl)-, or $R_6$ is an active ingredient, which requires help through a cell membrane, or a marker identical or different to $R_7$;
the recurrent units —(NR$_1$—R-A-R'—CO)—, are selected from the following groups:

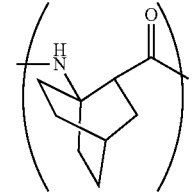

(II)

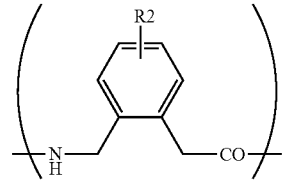

(V)

R2 = H
F
(C$_{1-6}$)-alkyl
OH
CN
C(=NH)NH$_2$
NH—C(=NH)NH$_2$
CF$_3$
CONH$_2$
(CH$_2$)$_3$—OH
(CH$_2$)$_3$—NH$_2$
CO$_2$H
CO-NH-(CH$_2$)$_3$-NH$_2$ n is a whole number comprised between 2 and 40;
said oligomer optionally contains $X_1$ and $X_2$,
in the case that $X_1$ and $X_2$ is present, $X_1$ and $X_2$ represent, independently from each other, a spacer group or a bond.

2. Oligomer represented by the generic formula (I):

$$R_6-X_1-(NR_1-R-A-R'-CO)_n-X_2-R_7 \quad (I)$$

at least one of $R_6$ and $R_7$ is a marker or an active ingredient selected from pepstatin or optionally substituted pepstatin; in the case where $R_6$ is an active ingredient, which requires help through a cell membrane, or a marker, $R_7$ is selected from hydroxy, $C_1$-$C_6$ alkoxy, aryl-($C_1$-$C_6$) alkoxy)- groups, or NH$_2$ or $R_7$ represents an active ingredient, which requires help through a cell membrane, or a marker identical or different to $R_6$; in the case where $R_7$ is an active ingredient, which requires help through a cell membrane, or a marker, $R_6$ is selected from a hydrogen atom, a $C_1$-$C_6$ alkyl group, an aryl group-($C_1$-$C_6$ alkyl)-, or $R_6$ is an active ingredient, which requires help through a cell membrane, or a marker identical or different to $R_7$; the recurrent units —($NR_1$—R-A-R'—CO)$_n$— are selected from the following groups:

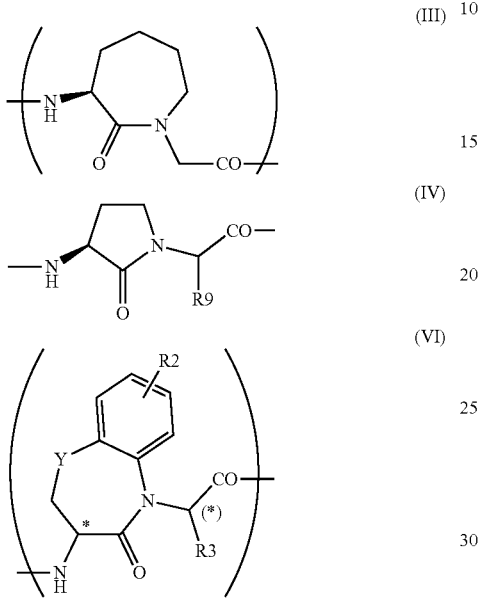

R2 = H
F
($C_{1-6}$)-alkyl
OH
CN
C(=NH)NH$_2$
NH—C(=NH)NH$_2$
CF$_3$
CONH$_2$
(CH$_2$)$_3$—OH
(CH$_2$)$_3$—NH$_2$
CO$_2$H
CO-NH·(CH$_2$)$_3$—NH$_2$ R3 = side chain of amino acids
Y = O
NH
S
CH$_2$ n is a whole number comprised between 2 and 40;
$X_1$ and $X_2$ each represent, independently from each other, a spacer group or a bond, and
$R_9$ represents a side chain of amino acids, except for $C_6H_5$—$CH_2$ when pepstatin is the active ingredient, and wherein the marker is selected from the group consisting of biotinyl markers, colored markers, markers with metal complexes, markers complexing with RNA or tRNA, markers with encapsulated xenon or for encapsulating xenon, fluorescein, sodium salt of fluorescein, 4',5'-Bis [N,N-bis(carboxymethyl)-5 amino methyl]fluorescein, 6-[fluorescein-5(6)-carboxamido]hexanoic acid, 6-[fluorescein-5(6)-carboxamido]hexanoic acid ester N-hydroxysuccinimide of fluorescein-5(6)-isothiocyanate, fluorescein-α-D-N-acetylneuraminide-polyacryl-amide, fluorescein amidite, fluorescein-di(β-D-galactopyranoside), fluorescein-di-(β-D-glucopyranoside), fluorescein diacetate, fluorescein-5 (6)-isothiocyanate diacetate, fluorescein-5-maleimide diacetate, fluorescein-6-isothiocyanate diacetate, fluorescein dibutyrate, fluorescein dilaurate, diphosphate salt of triammonium fluorescein, fluorescein hyaluronic acid, isomer I of fluorescein isothiocyanate, mercuryfluorescein acetate, mono-p-guanidinobenzoate-fluorosuccinic hydrochlorate, fluorescein O,O'-diacrylate hydrochlorate, fluorescein O,O'-dimethacrylate, fluorescein o-acrylate, fluorescein O-methacrylate, N-hydroxysuccinimide fluorescein ester, fluorescein-5-thiosemicarbazide, fluorescein-α-D-galactosamine polyacrylamide, fluorescein-α-D-mannopyranosidepolyacrylamide, 4(5)-(iodoacetamido)-fluorescein, 5-(Bromomethyl)fluorescein, 5-(Iodoacetamido) fluorescein, diacetate of the ester of N-succinimidyl-5-Carboxy-fluorescein, diacetate of the ester of N-succinimidyl-6-carboxy-fluorescein, aminophenyl-fluorescein, Biotin-4-fluorescein, hydroxyphenyl-fluorescein, MTS-4-fluorescein, poly(fluorescein-isothiocyanate allylamine) hydrochlorate, poly(fluoresccine-O-acrylate), poly(fluorescein-O-methacrylate), PPHT-fluorescein acetate, 5([4,6-dichlorotriazin-2-yl]amino) fluorescein hydrochlorate, 6-([4,6-dichlorotriazin-2-yl]amino) fluorescein hydrochlorate, poly[(methylmethacrylate)-co-(fluorescein-O-methacrylate)], poly[methylmethacrylate-co-(fluorescein O-acrylate)], 5(6)-(Biotinamidohexanoylamido)pentyhhioureidylfluorescein, N-(5-fluoresceinyl)maleimide, disodium salt of Mercury-dibromo-fluorescein, fluorescein-di-[methylene-N-methylglycine], disodium salt of 2',4',5',7-tetrakis-(acetoxymercuro)-fluoroscein, erythrosin B, ethyl eosin, 5-carboxy fluorescein, ester N-succinimidyl of 5-carboxy fluorescein ester perchlorate, rhodamine B octadecyl, N-hydroxysuccinimide ester of 6-Carboxyfluorescein, dibenzyl fluorescein, rhodol, 6-amino fluorescein, rhodamine 6G, rhodamine B and rhodamine 123.

3. Oligomer according to claim 1, characterised in that the spacer groups $X_1$ or $X_2$ is selected from the following groups:

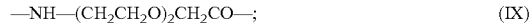

—NH—(CH$_2$CH$_2$O)$_2$CH$_2$CO—; (IX)

—NH—(CH$_2$)$_5$CO— (X).

4. Oligomer according to claim 2, characterised in that the spacer groups $X_1$ or $X_2$ is selected from the following groups:

—NH—(CH$_2$CH$_2$O)$_2$CH$_2$CO—; (IX)

—NH—(CH$_2$)$_5$CO— (X).

5. A pharmaceutical composition comprising an oligomer according to claim 1.

6. A pharmaceutical composition comprising an oligomer according to claim 2.

7. A method of facilitating entry of an active ingredient (AI) into biological cells; which comprises contacting said cells with an oligomer according to claim 1.

8. A method of facilitating entry of an active ingredient (AI) into biological cells; which comprises contacting said cells with an oligomer according to claim 2.

9. Method of preparing an oligomer according to claim 1, characterised by the following successive steps:
a) polymerisation by a strategy of peptide synthesis on solid support, comprising the reaction of the constrained dipeptide or tripeptide mimic unit of following formula (XI'):

P—NR$_1$—R-A-R'—CO—OH (XI')

in which the group P is an N-protector group, to the recurrent unit —NR$_1$—R-A-R'—CO— followed by deprotection to synthesize the following product (XII):

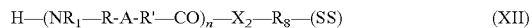

H—(NR$_1$—R-A-R'—CO)$_n$—X$_2$—R$_8$—(SS) (XII)

in which, n and $X_2$ are as defined in claim 1;

$R_8$ is a precursor group of $R_7$ before cleavage, $R_7$ is as defined in claim 1;

(SS) is the solid support;

a2) optionally, if $X_1$ is not a bond, coupling reaction between P—$X_1$—OH, in which the group P is an N-protector group and $X_1$ is as defined in claim 1, and the N-terminal amine of the product (XII), followed by a step of de-protection of the N-terminal extremity to synthesise the following product (XII'):

H—$X_1$—(NR$_1$—R-A-R'—CO)$_n$—$X_2$—$R_8$—(SS)     (XII')

b) coupling reaction between an active ingredient (AI) and the N-terminal amine of the product (XII'), to synthesise the following, product (XIII):

(AI)—$X_1$—(NR$_2$—R-A-R'—CO)$_n$—$X_2$—$R_8$—(SS)     (XIII)

in which, (AI) is as defined in claim 1, c) a cleavage reaction making it possible to free the oligomer of formula (I) from the solid support from the product of formula (XIII).

10. Method of preparing an oligomer according to claim 2, characterised by the following successive steps:

b) polymerisation by a strategy of peptide synthesis on solid support, comprising the reaction of the constrained dipeptide or tripeptide mimic unit of following formula (XI'):

P—NR$_1$—R-A-R'—CO—OH     (XI')

in which the group P is an N-protector group, to the recurrent unit —NR$_1$—R-A-R'—CO— followed by deprotection to synthesize the following product (XII):

H—(NR$_1$—R-A-R'—CO)$_n$—$X_2$—$R_8$—(SS)     (XII)

in which, n and $X_2$ are as defined in claim 2;

$R_8$ is a precursor group of $R_7$ before cleavage, $R_7$ is as defined in claim 2;

(SS) is the solid support;

a2) optionally, if $X_1$ is not a bond, coupling reaction between P—$X_1$—OH, in which the group P is an N-protector group and $X_1$ is as defined in claim 2, and the N-terminal amino of the product (XII), followed by a step of de-protection of the N-terminal extremity to synthesise the following product (XII'):

H—$X_1$—(NR$_1$—R-A-R'—CO)$_n$—$X_2$—$R_8$—(SS)     (XII')

b) coupling reaction between an active ingredient (AI) and the N-terminal amino of the product (XII'), to synthesise the following product (XIII):

(AI)—$X_1$—(NR$_2$—R-A-R'—CO)$_n$—$X_2$—$R_8$—(SS)     (XIII)

in which, (AI) is as defined in claim 2, c) a cleavage reaction making it possible to free the oligomer of formula (I) from the solid support from the product of formula (XIII).

11. Method according to claim 9, characterised by a step (a1) prior to step (a) of coupling of a spacer group $X_2$ on the solid support.

12. Method according to claim 10, characterised by a step (a1) prior to step (a) of coupling of a spacer group $X_2$ on the solid support.

13. Method of preparing a vectorized active ingredient (AI) which comprises bonding an active ingredient (AI) to $X_1$ and/or $X_2$ of an oligomer of formula I':

—$X_1$—(NR$_1$—R-A-R'—CO)$_n$—$X_2$—     I' the recurrent units —(NR$_1$—R-A-R'—CO)—, are selected from the following groups:

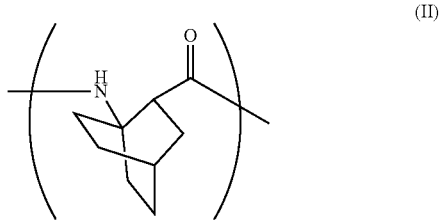
(II)

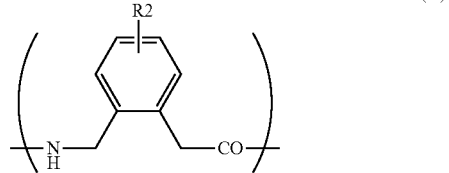
(V)

R2 = H
F
$(C_{1-6})$-alkyl
OH
CN
C(=NH)NH$_3$
NH—C(=NH)NH$_2$
CF$_3$
CONH$_2$
(CH$_2$)$_3$—OH
(CH$_2$)$_3$—NH$_2$
CO$_2$H
CO—NH—(CH$_2$)$_n$—NH$_2$ n is a whole number comprised between 2 and 40;

$X_1$ and $X_2$, represent, independently of each other, a spacer group or a bond.

14. Method of preparing a vectorized active ingredient (AI) which comprises bonding an active ingredient (AI) to $X_1$ and/or $X_2$ of an oligomer of formula I':

—$X_1$—(NR$_1$—R-A-R'—CO)$_n$—$X_2$—     I' the recurrent units —(NR$_1$—R-A-R'—CO)—, are selected from the following groups:

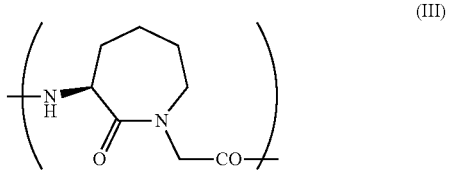
(III)

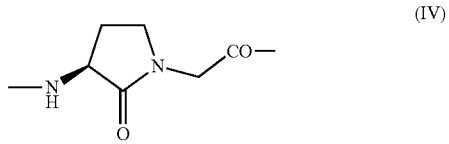
(IV)

$$\text{(VI)}$$

R2 = H, F, (C$_{1-6}$)-alkyl, OH, CN, C(=NH)NH$_2$, NH—C(=NH)NH$_2$, CF$_3$, CONH$_2$, (CH$_2$)$_3$—OH, (CH$_2$)$_3$—NH$_2$, CO$_2$H, CO-NH-(CH$_2$)$_3$-NH$_2$ R3 = side chain of amino acids

Y = O, NH, S, CH$_2$ n is a whole number comprised between 2 and 40;

X$_1$ and X$_2$, represent, independently of each other, a spacer group or a bond.

15. Method according to claim 13, characterised in that the active ingredient is a medicine approved for treating a disease selected from the group of consisting of lysosomal diseases, cancer, and Alzheimer's disease.

16. Method according to claim 14, characterised in that the active ingredient is a medicine approved for treating a disease selected from the group of consisting of lysosomal diseases, cancer, and Alzheimer's disease.

17. Method according to claim 13, characterised in that n is comprised between 4 and 8.

18. Method according to claim 14, characterised in that n is comprised between 4 and 8.

19. Method according to claim 13, characterised in that the spacer groups X$_1$ and X$_2$, independently one from each other are a bond or selected from the following groups:

—NH—(CH$_2$CH$_2$O)$_2$CH$_2$CO—;  (IX)

—NH—(CH$_2$)$_5$CO—  (X).

20. Method according to claim 14, characterised in that the spacer groups X$_1$ and X$_2$, independently one from each other are a bond or selected from the following groups:

—NH—(CH$_2$CH$_2$O)$_2$CH$_2$CO—;  (IX)

—NH—(CH$_2$)$_5$CO—  (X).

21. The oligomer according to claim 1, wherein the active ingredient is pepstatin.

* * * * *